United States Patent [19]

Sauer et al.

[11] Patent Number: 5,697,943
[45] Date of Patent: Dec. 16, 1997

[54] APPARATUS AND METHOD FOR PERFORMING COMPRESSIONAL ANASTOMOSES

[75] Inventors: Jude S. Sauer, Pittsford; Roger J. Greenwald, Holley; Theodore J. Tiberio, Hilton; Jeffrey M. Shaw, Livonia; John F. Hammond, Canadaigua, all of N.Y.

[73] Assignee: United States Surgical Corporation, Norwalk, Conn.

[21] Appl. No.: 561,678

[22] Filed: Nov. 22, 1995

Related U.S. Application Data

[62] Division of Ser. No. 151,614, Nov. 12, 1993, Pat. No. 5,503,635.
[51] Int. Cl.⁶ .................................................. A61B 17/00
[52] U.S. Cl. ................................... 606/153; 606/151
[58] Field of Search ............................. 606/151, 153, 606/154, 139, 150; 623/1, 12

[56] References Cited

U.S. PATENT DOCUMENTS

| | | |
|---|---|---|
| 2,453,056 | 11/1948 | Zack . |
| 3,155,095 | 11/1964 | Brown . |
| 3,265,069 | 8/1966 | Healy et al. . |
| 3,316,914 | 5/1967 | Collito . |
| 3,774,615 | 11/1973 | Lim et al. . |
| 3,974,835 | 8/1976 | Hardy, Jr. . |
| 4,055,186 | 10/1977 | Leveen . |
| 4,214,586 | 7/1980 | Mericle . |
| 4,467,804 | 8/1984 | Hardy et al. . |
| 4,552,148 | 11/1985 | Hardy, Jr. et al. . |
| 4,567,891 | 2/1986 | Kanshin et al. . |
| 4,598,712 | 7/1986 | Rebuffat et al. . |
| 4,624,257 | 11/1986 | Berggren et al. ............... 606/153 |
| 4,630,608 | 12/1986 | Arroyo . |
| 4,632,435 | 12/1986 | Polyak . |
| 4,667,673 | 5/1987 | Li ................................. 606/153 |
| 4,681,108 | 7/1987 | Rosati et al. ..................... 606/151 |
| 4,752,024 | 6/1988 | Green et al. . |
| 4,903,697 | 2/1990 | Resnick et al. . |
| 4,907,591 | 3/1990 | Vasconcellos et al. ........... 606/154 |
| 4,917,087 | 4/1990 | Walsh et al. . |
| 4,931,057 | 6/1990 | Cummings et al. . |
| 4,957,499 | 9/1990 | Lipatov et al. . |
| 4,964,863 | 10/1990 | Kanshin et al. . |
| 4,966,602 | 10/1990 | Rebuffat et al. . |
| 5,254,127 | 10/1993 | Wholey et al. . |
| 5,282,810 | 2/1994 | Allen et al. . |
| 5,290,298 | 3/1994 | Rebuffat et al. . |
| 5,346,501 | 9/1994 | Regula et al. . |
| 5,425,738 | 6/1995 | Gustafson et al. ............... 606/153 |
| 5,464,415 | 11/1995 | Chen .............................. 606/153 |

FOREIGN PATENT DOCUMENTS

| | | |
|---|---|---|
| 0517488 | 12/1992 | European Pat. Off. . |
| 1537228 | 1/1990 | U.S.S.R. . |
| 9320757 | 10/1993 | WIPO . |

OTHER PUBLICATIONS

Rebuffat et al., Clinical Application of a New Compression Anastomotic Device for Colorectal Surgery, The American Journal of Surgery, vol. 159, pp. 330–335, Mar. 1990.

Rosati et al., A New Mechanical Device for Circular Compression Anastomosis, Ann. Surg., vol. 207, No. 3, pp. 245–253, Mar. 1988.

*Primary Examiner*—Jeffrey A. Schmidt

[57] ABSTRACT

A surgical instrument for carrying and attaching separate components of a compression anastomosis device to the end of tissue of a tubular hollow organ, which includes an elongated housing having a proximal end and a distal end; first and second compression anastomosis device components; a supporting member operatively associated with the distal end of the elongated housing, for supporting the first and second compression anastomosis device components; and assembling structure associated with the supporting member and operable from the proximal end of the elongated housing, for assembling the first and second compression anastomosis device components within tubular body tissue.

10 Claims, 32 Drawing Sheets

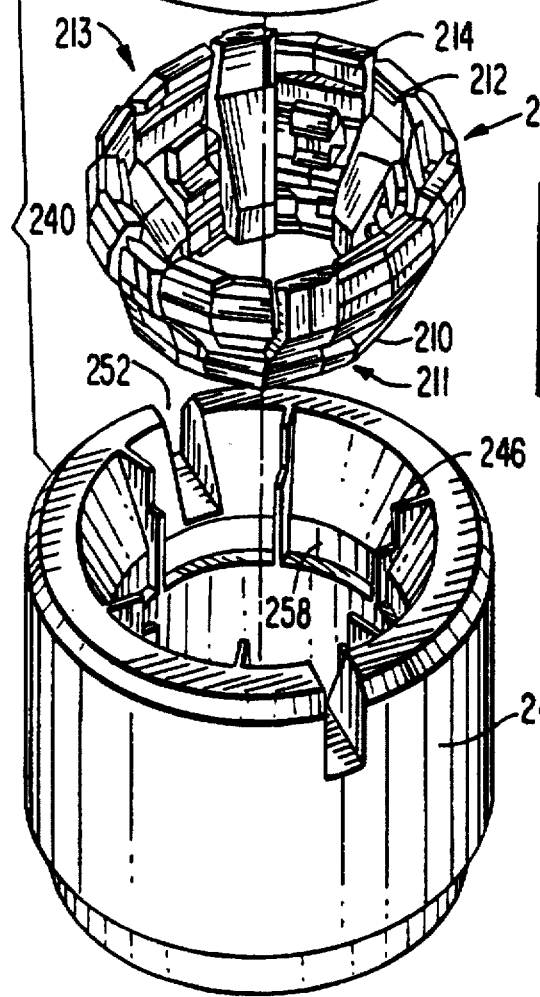
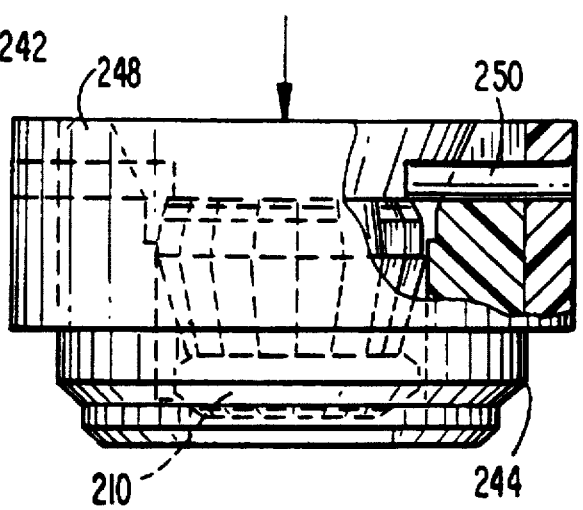
FIG.2A
FIG.2B

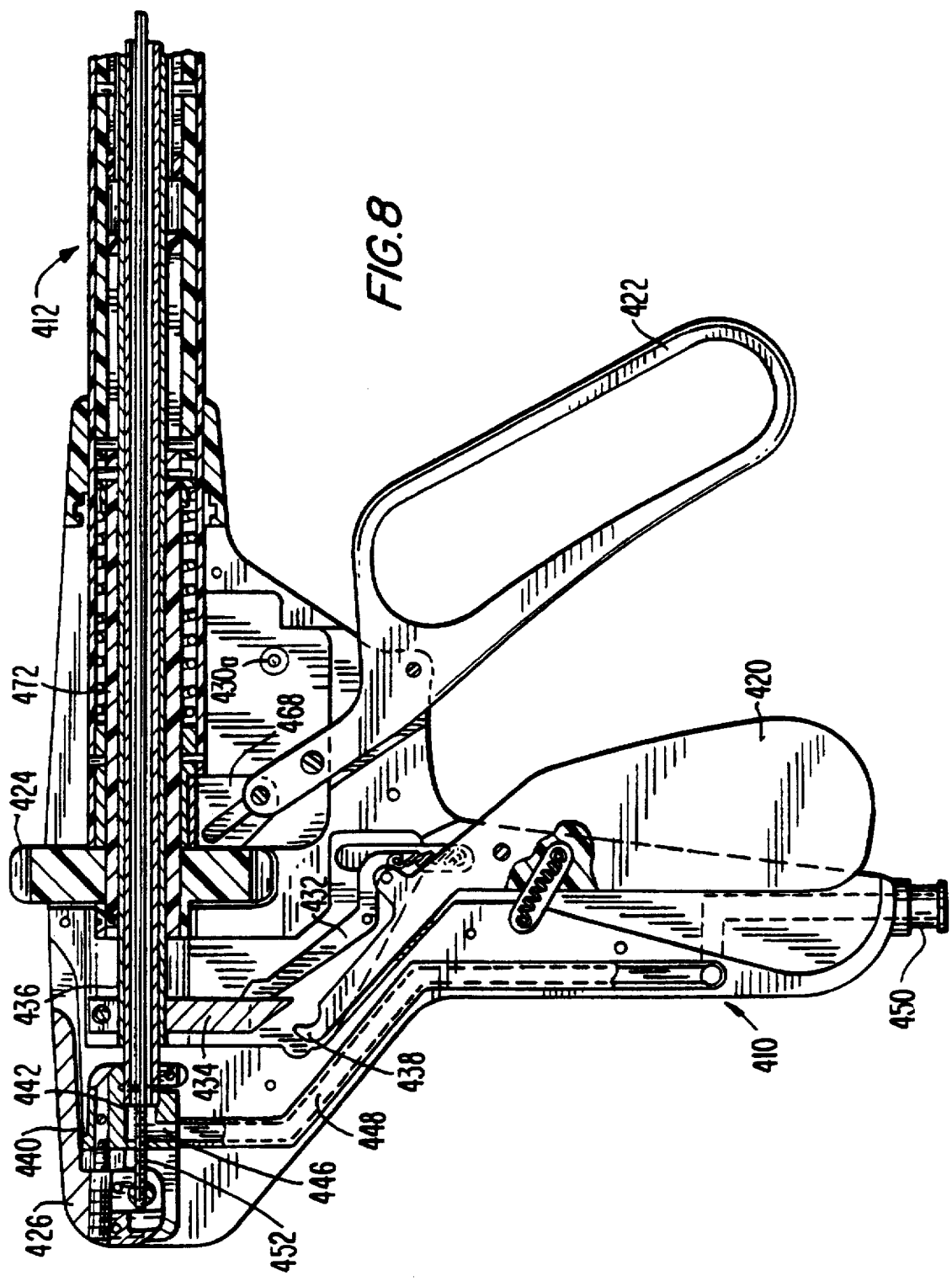

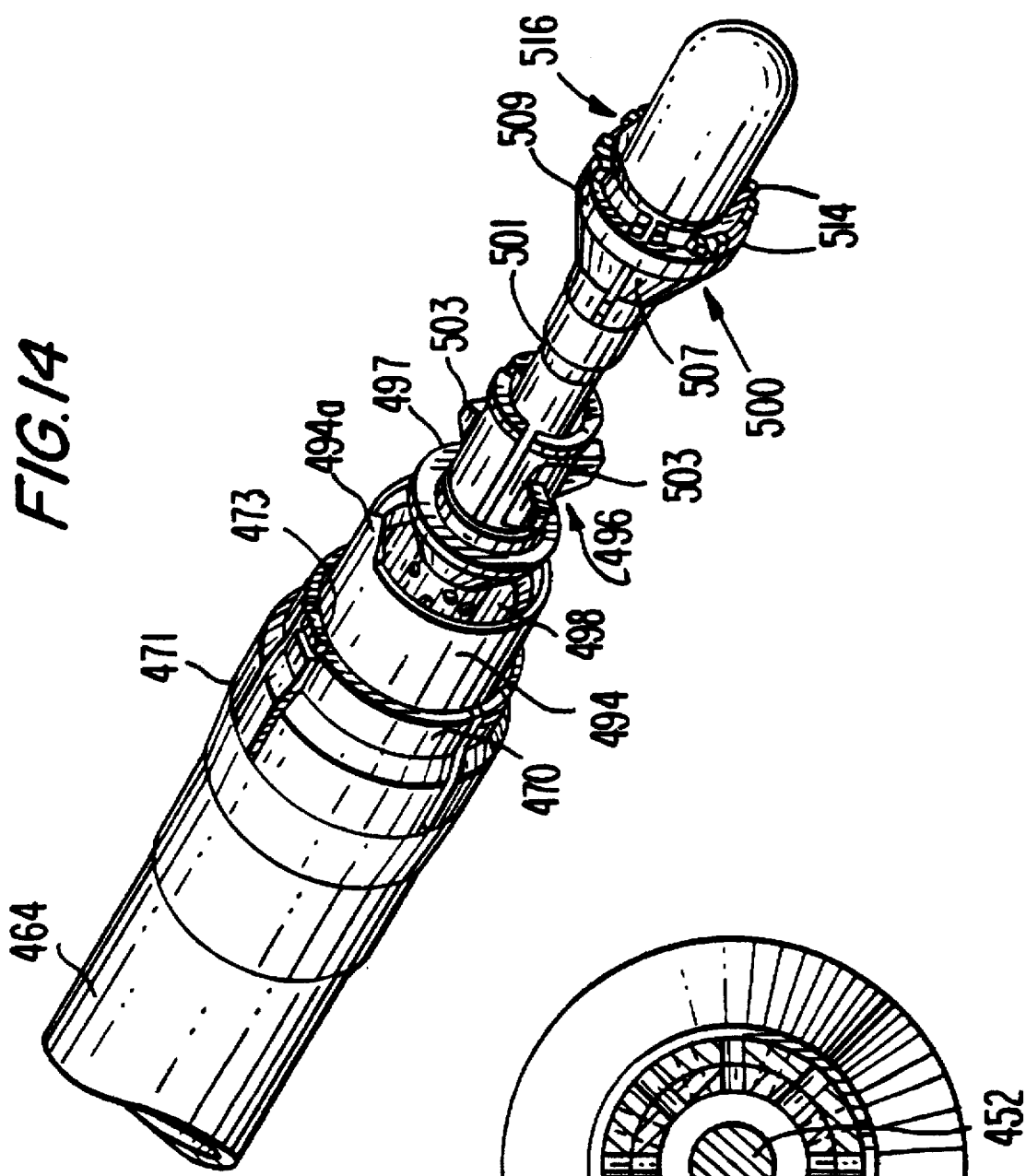

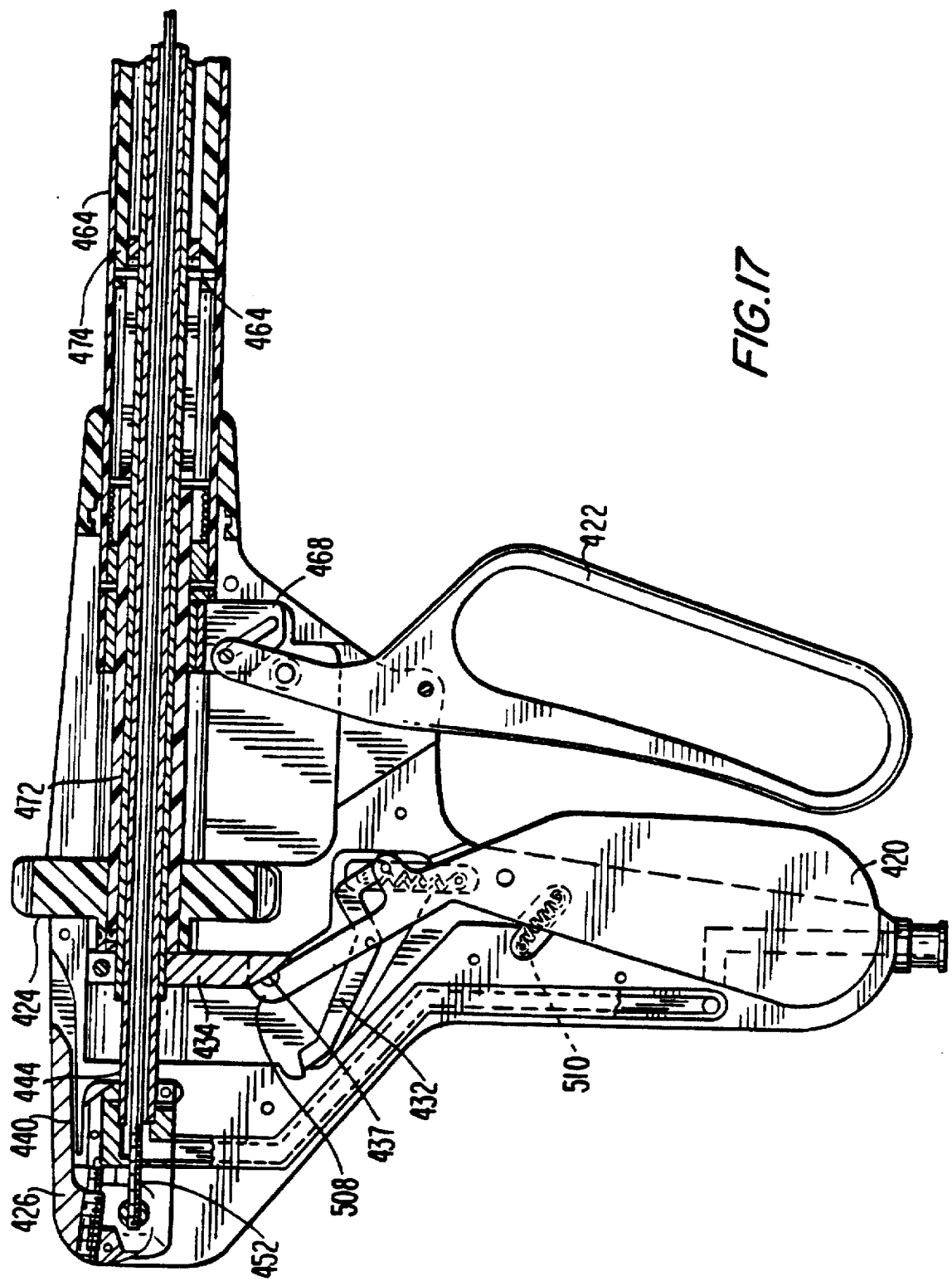

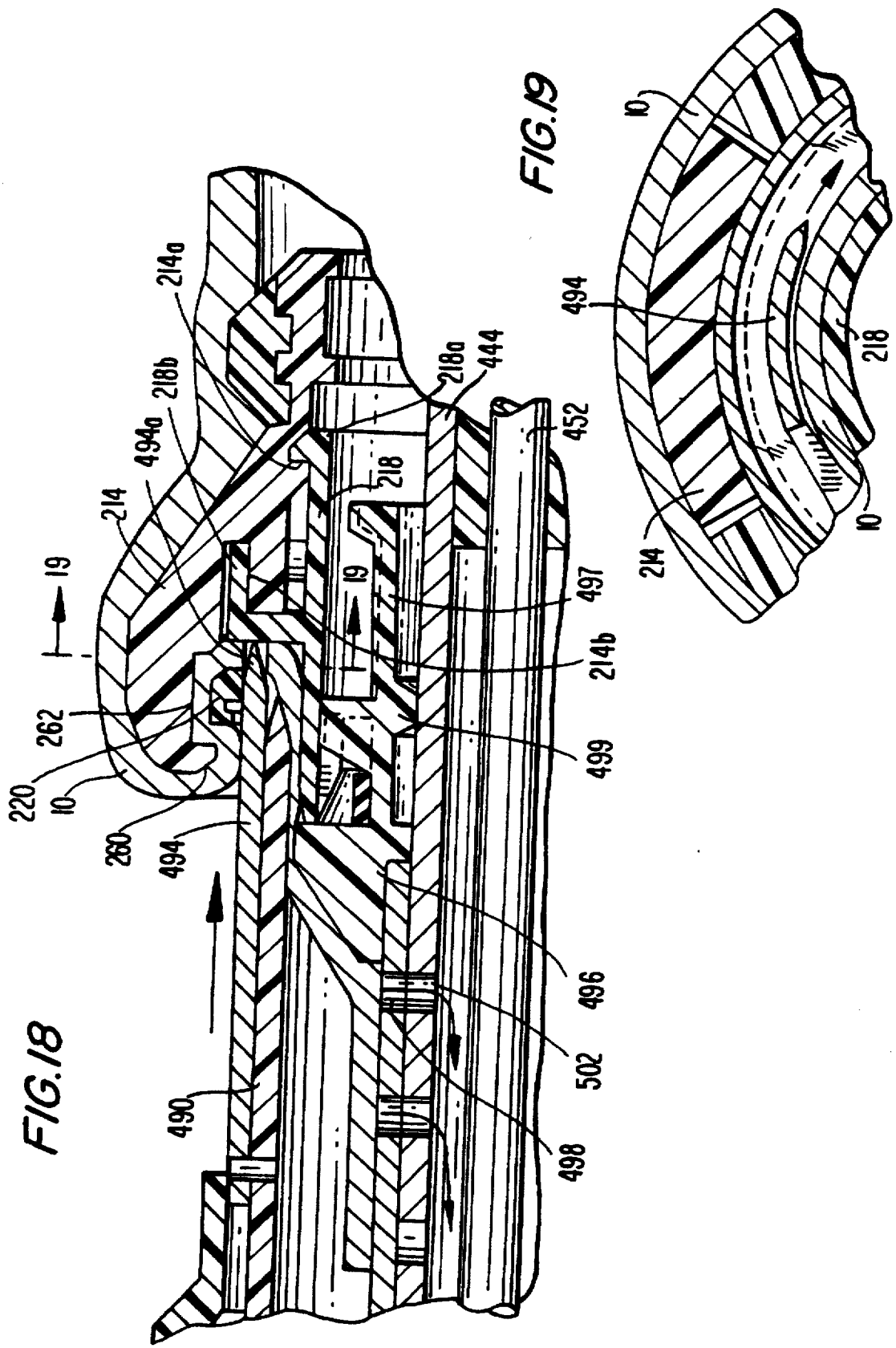

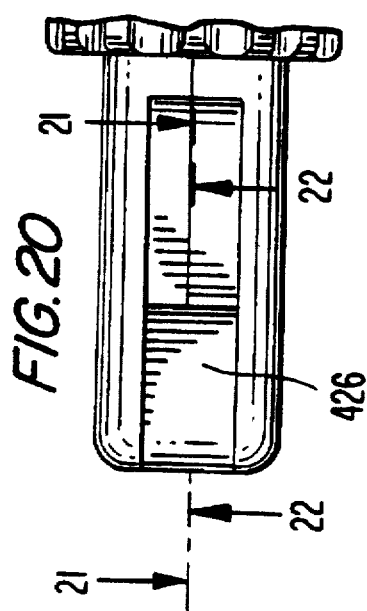
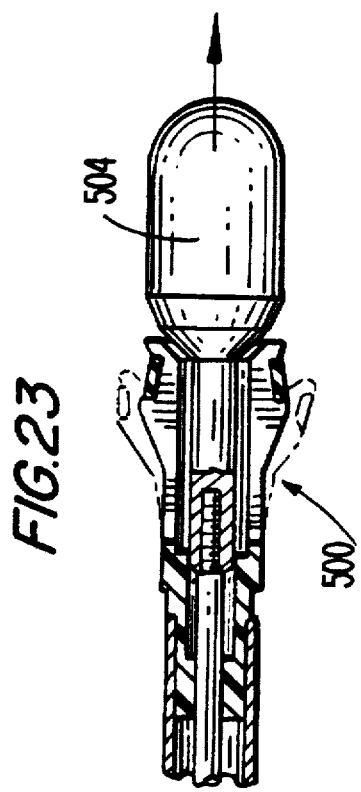
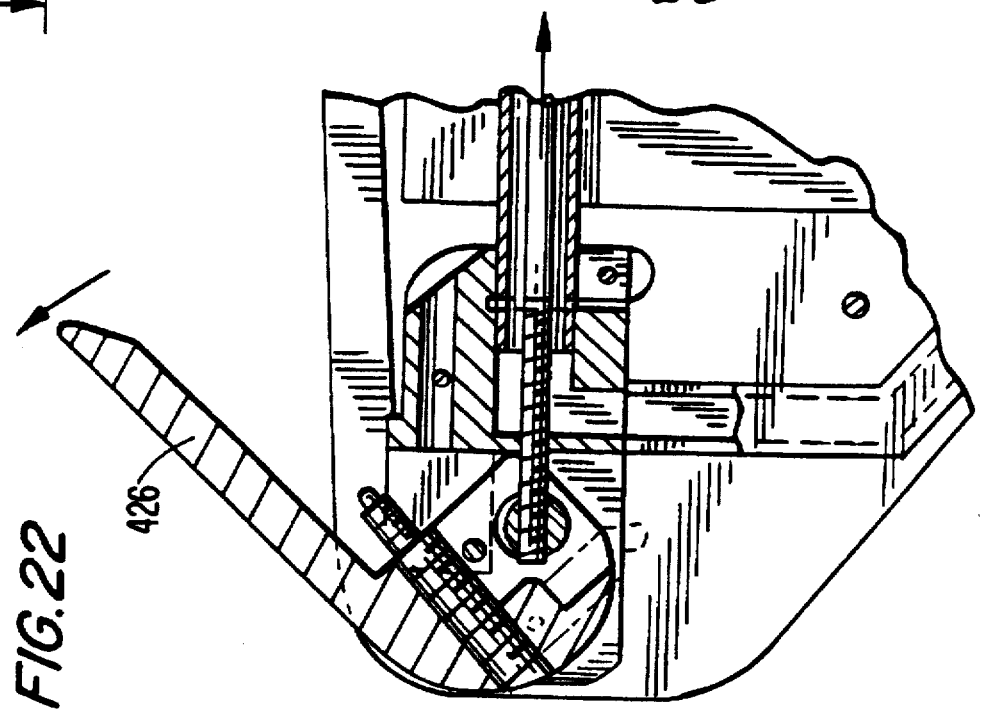

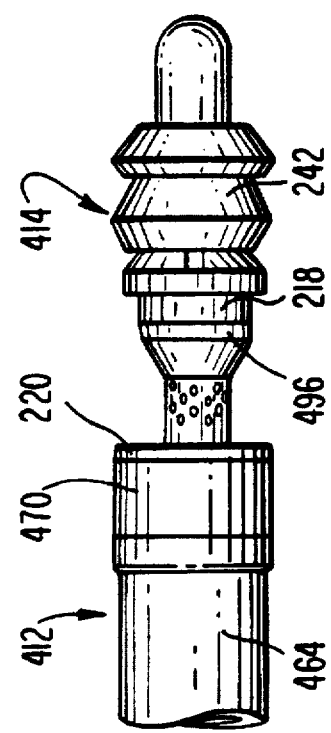
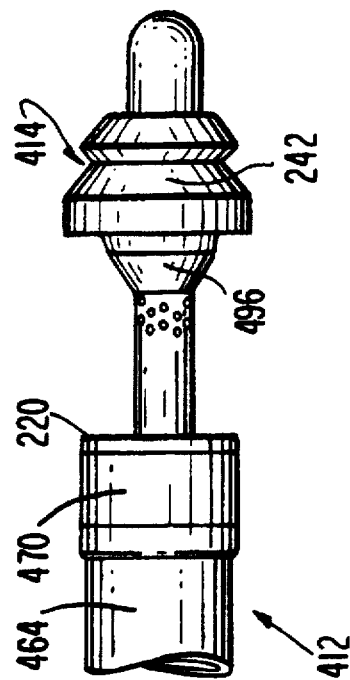
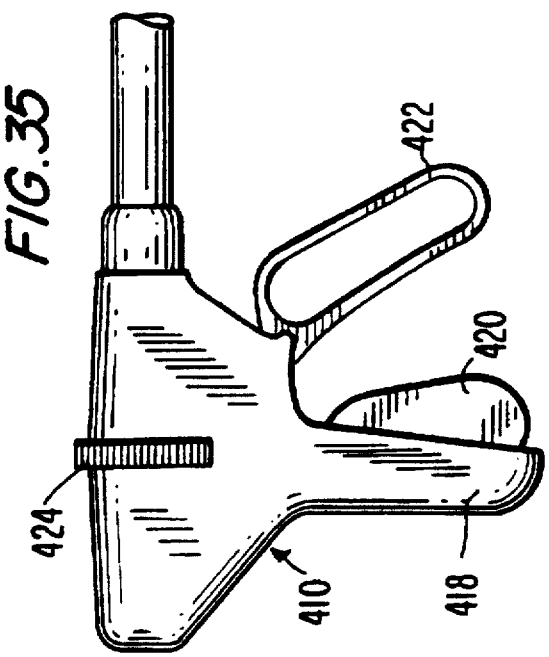
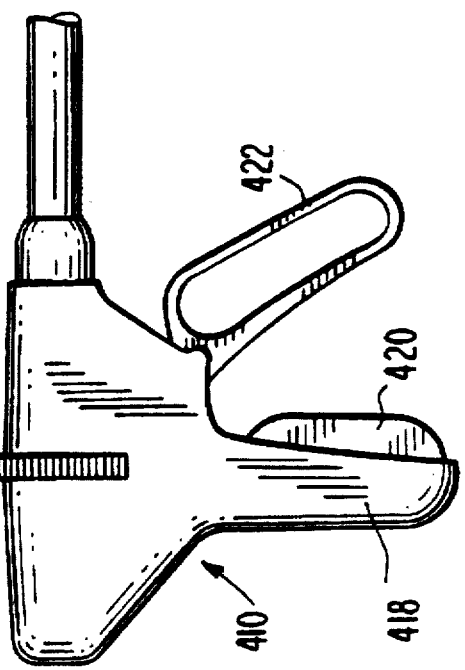

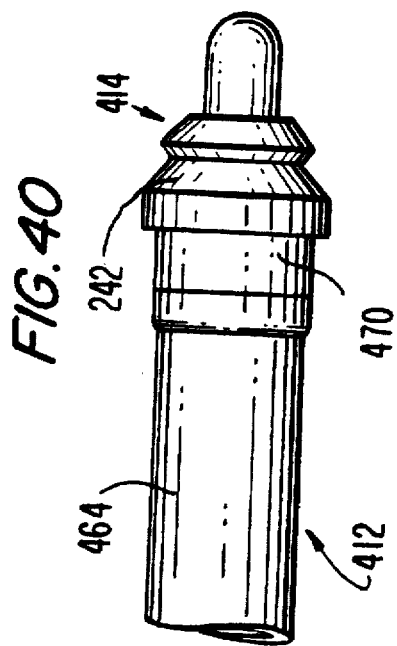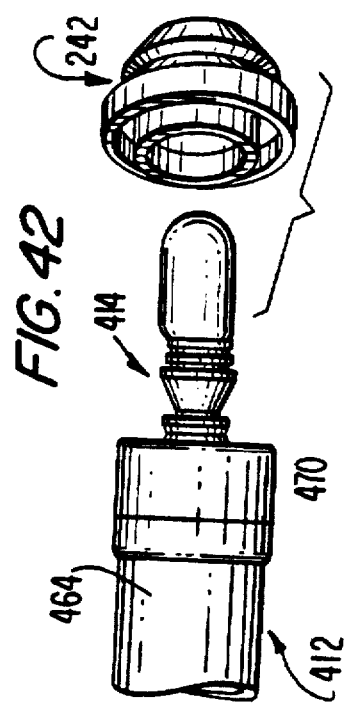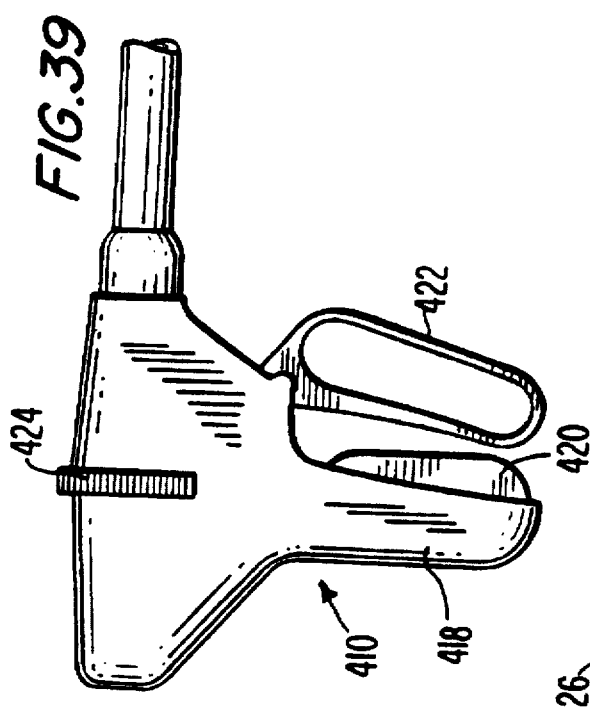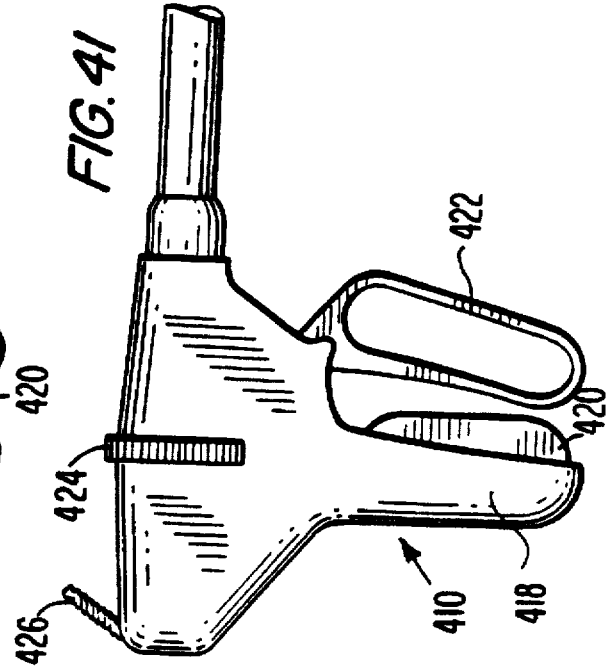

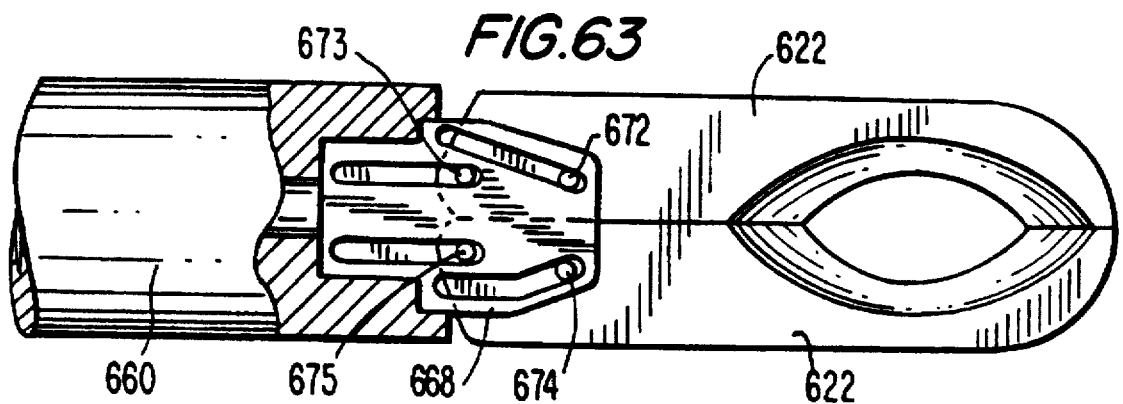
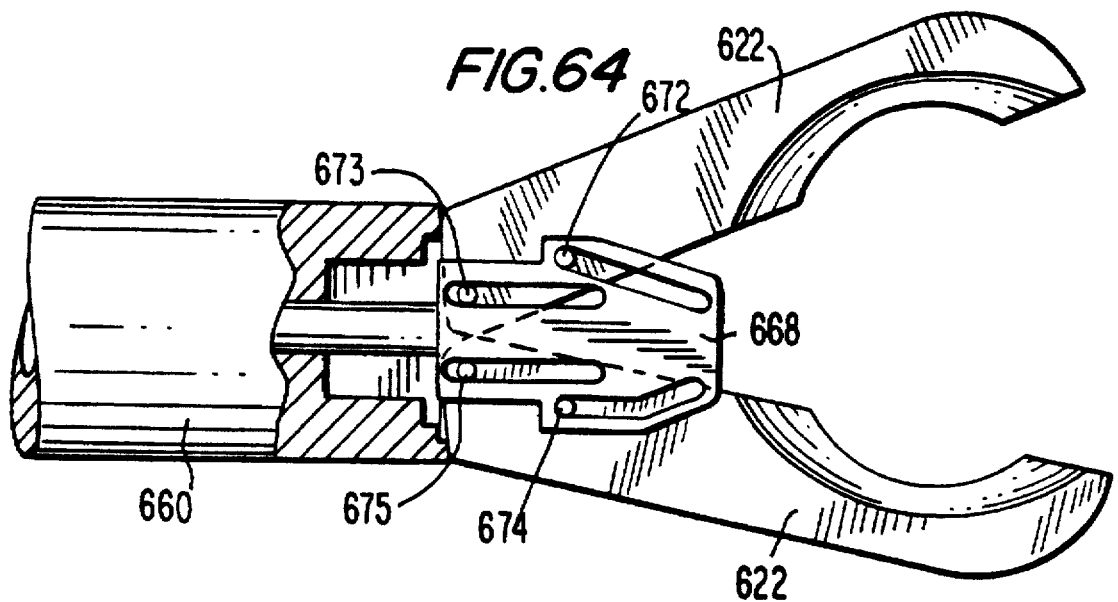
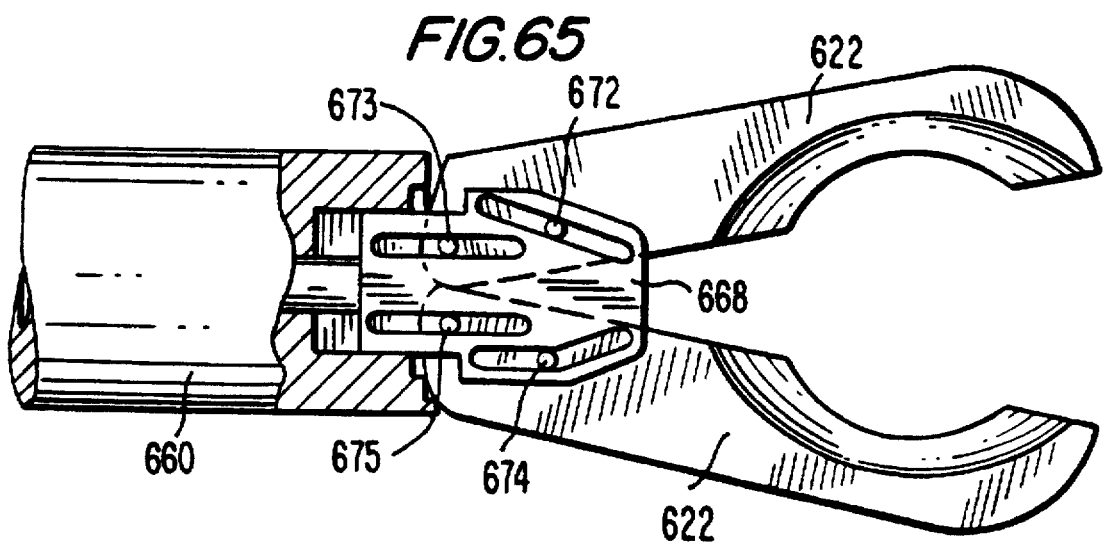

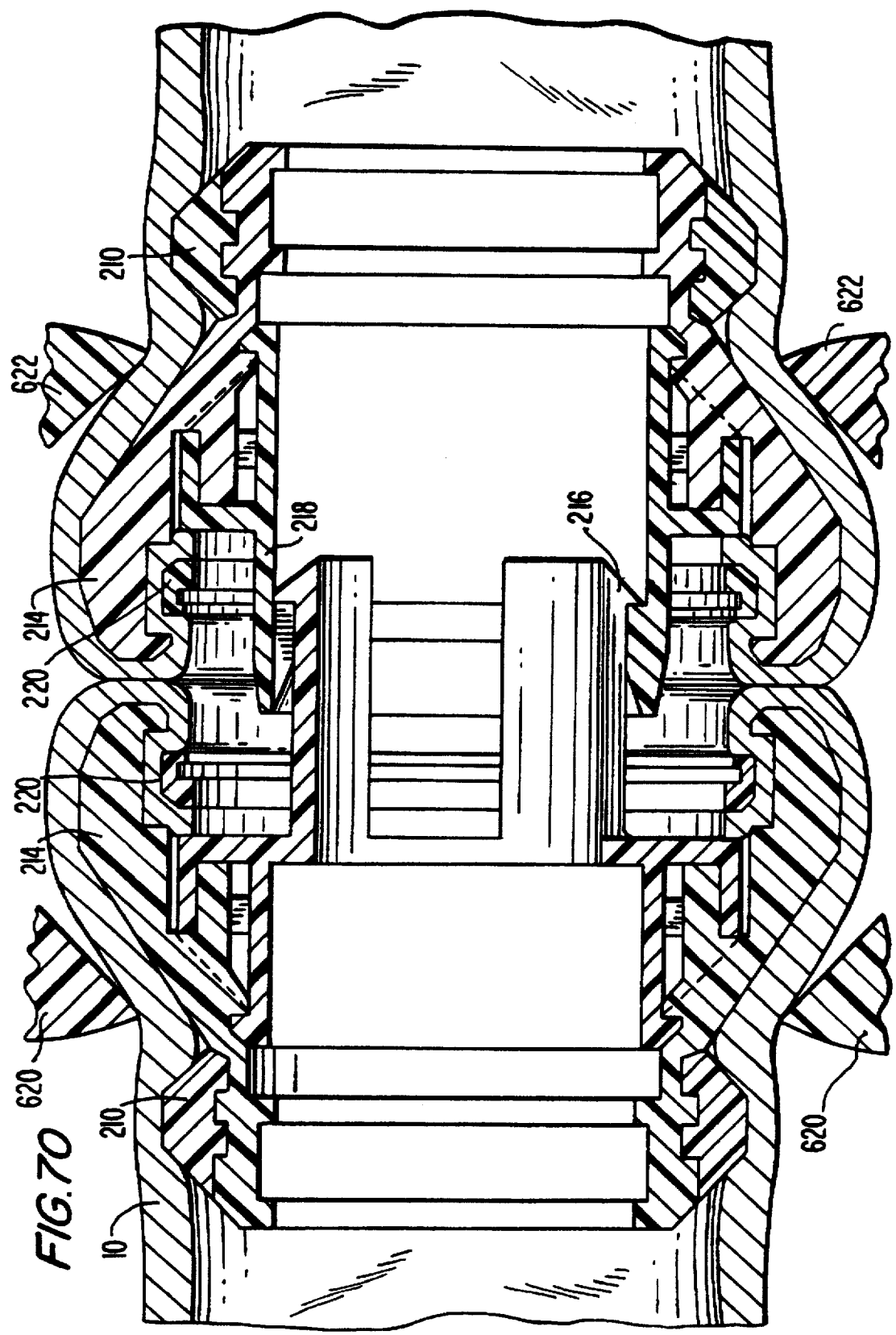

APPARATUS AND METHOD FOR PERFORMING COMPRESSIONAL ANASTOMOSES

This is a divisional of U.S. application Ser. No. 08/151,614 filed Nov. 12, 1993, now U.S. Pat. No. 5,503,635.

BACKGROUND OF THE INVENTION

1. Field of the Invention

The present invention relates to apparatus and method for performing circular end-to-end compression anastomoses and more particularly, to apparatus and method for performing compression anastomoses endoscopically.

2. Description of the Related Art

Performing anastomoses to connect tissue within the body is well-known in the art. For example, circular end-to-end anastomoses are commonly performed to join together the ends of hollow organs such as the intestines. Typically, a diseased or blocked portion of the intestine is cut-out and the healthy ends joined together. One method of performing anastomoses involves the use of compression members which compress the ends of the hollow sections to be joined together, thereby allowing a natural anastomosis to occur in the tissue adjacent the compressed tissue. After a period of time, due to necrosis of the compressed edges, the compression devices fall inside the intestine and are then evacuated therefrom during normal excretion of waste. Compression anastomoses have typically been performed by gaining access to the surgical site either rectally or through open surgery. In the case of the rectally performed procedures, anastomosis is limited to the most distal tracts of the intestine. In the case of open surgery to place compression members, the patient's recovery is lengthened due to the extensive healing required of the incisions made to access the surgical site.

Another method of performing anastomoses involves the use of a circular stapling device which applies an annular array of staples to join the ends of hollow organs. A common procedural step of forming an anastomosis, either using a circular stapler or with other known methods and apparatus, is to apply a "purse string" suture to each of the ends to be anastomosed. The "purse string" suture is utilized to draw the ends of the hollow organ closed so that, inter alia, a complete anastomosis is formed when the ends of the organ are joined either by compression devices or by a surgical stapling device.

In laparoscopic procedures, surgery is performed in the interior of the abdomen through small incisions; in endoscopic procedures, surgery is performed in any hollow viscus of the body through narrow endoscopic tubes inserted through natural orifices. Laparoscopic procedures generally require that any instrumentation inserted into the body be sealed, i.e. provisions must be made to ensure that gases do not enter or exit the body through the laparoscopic incision or instruments as, for example, in surgical procedures in which the surgical region is insufflated. Moreover, laparoscopic and endoscopic procedures often require the surgeon to act on organs, tissues and vessels deep within the body, thereby requiring that any instruments be used in such procedures be long and narrow while being functionally controllable from the end of the instrument outside the patient's body, i.e. the proximal end. Typically, in laparoscopic and endoscopic procedures, patient recovery time is several days or weeks shorter than that for conventional invasive surgical procedures.

A need presently exists for apparatus and methods which facilitate performing anastomoses through small incisions using compression anastomosis devices which fit through cannulas of lesser diameter than the hollow organ to be anastomosed. That is, a need presently exists for apparatus and methods capable of performing compressional anastomoses endoscopically or laparoscopically so as to both increase the versatility of the procedure and reduce patient recovery time.

An additional need exists for alternative apparatus and method which will perform the function performed by "purse stringing" the ends of hollow organs to be anastomosed.

SUMMARY OF THE INVENTION

The present invention provides novel apparatus and method for compression anastomoses. A compression device is provided for the anastomosis of a hollow organ and includes a first collapsible member movable between an expanded configuration and a collapsed configuration, the first collapsible member having a longitudinal bore defined by an inner surface; a first mating member; locking means disposed on the first collapsible member for locking the first collapsible member with the first mating member; a second collapsible member movable between an expanded configuration and a collapsed configuration, the second collapsible member having a longitudinal bore defined by an inner surface; a second mating member; locking means disposed on the second collapsible member for locking the second collapsible member with the second mating member; and the first member adapted to interlock with the second member; whereby when the first and second collapsible members are in the collapsed configurations, the collapsible members are configured and dimensioned such that they are insertable in a cannula for placement in the open ends of a hollow organ.

Preferably, at least one of the first and the second collapsible members includes a plurality of adjacent finger members. In an alternate embodiment, at least some of the finger members are permanently joined together in a predetermined spatial relationship. The device may further comprise clamping means associated with the finger members, for clamping the finger members together. The clamping means preferably includes an annular ring configured and dimensioned to hold the finger members together.

In one embodiment, either the first or the second mating members includes an axle member having latching means disposed thereon for interlocking with the locking means. Preferably, at least one of the collapsible members is made from either partially or totally bioabsorbable or biofragmentable materials.

Holding means are provided on the first and second collapsible members for holding the collapsible members in a collapsed position. Additionally, a tissue retaining member adapted for insertion into either or both, the first and second collapsible members, thereby exerting an outwardly directed force on an inside perimeter of the first collapsible member when tissue of the hollow organ is locked between the tissue retaining member and the inside perimeter of the first collapsible member. The tissue retaining member is preferably an annular ring.

In one embodiment, the first and/or the second collapsible members comprise an annular base having finger members extending from the annular base, the annular base having the same shape in the expanded and collapsed configuration.

A surgical instrument for carrying and attaching separate components of a compression anastomosis device to the end of tissue of a hollow organ, is provided which includes an elongated housing having a proximal end and a distal end;

supporting means operatively associated with the distal end of the elongated housing, for supporting and aligning a plurality of compression anastomosis device components; assembling means associated with the supporting means, for assembling at least two of the compression anastomosis device components; actuating means operatively connected to the proximal end of the elongated housing, for selectively actuating the assembling means such that the assembling means travels a predetermined distance in a first direction and then travels a predetermined distance in a second direction; and driving means associated with the distal end of the elongated housing, for driving at least one of said compression anastomosis device components such that said separate components become attached to the end of said hollow organ.

In an alternate embodiment, cutting means are provided and are operatively mounted at the distal end of the elongated housing means, for selectively cutting away excess tissue.

The supporting means may include at least one retaining portion for releasably retaining at least one of the compression anastomosis device components. The retaining portion may include at least one expandable member movable between a holding position and a released position, the expandable member being configured and dimensioned to releasably retain at least one of the compression anastomosis device components. The at least one expandable member preferably includes a plurality of radially expandable elements. Release control means, operable from the proximal end of the elongated housing, for controlling the at least one expandable member between the holding position and the released position are also preferably provided.

The present invention further provides a surgical device for approximating surgical implant device components inserted within a cavity of a body. The device includes an elongated housing; and at least two grasping means operatively attached to the elongated housing, each of the grasping means being operable between an open position and a closed position, for receiving and grasping surgical implant device components; whereby at least one of the at least two grasping means are further movable toward and away from the other of the at least two grasping means, between a first position for receiving the surgical implant device components and a second position for joining the surgical implant device components.

The approximating device may further comprise positioning means operatively associated with each of the at least two grasping means for positioning the grasping means at a predetermined position between the open and closed positions. Alternatively, each of the at least two grasping means includes a pair of finger members configured and dimensioned to releasably hold the surgical implant device components. Closure controlling means may also be provided which are operatively associated with each pair of finger members for controlling the closure of each finger of the pair of finger members such that closure of each of the finger members of the pair of finger members travels a predetermined distance independent of the other finger of the pair of fingers.

In one embodiment of the approximating device, actuating means are operatively connected to the proximal end of the elongated housing means for selectively actuating opening and closing of the grasping means.

A method for forming a compression anastomosis is provided and comprises the steps of providing a compression device for the anastomosis of hollow organs, the device including at least two collapsible components; providing a surgical instrument for carrying and attaching the separate components of the compression anastomosis device to the ends of hollow tissue sections; providing a surgical device for approximating compression anastomosis device components which includes elongated housing means; and at least two grasping means operatively attached to the elongated housing member, each of the grasping means being operable between an open position and a closed position, for receiving and grasping compression anastomosis device components; whereby at least one of the at least two grasping means are further movable toward and away from the other of the at least two grasping means, between a first position for receiving the compression anastomosis device components and a second position for joining the compression anastomosis device components; inserting the first and second collapsible members in open ends of hollow tissue sections to be joined using the surgical instrument for carrying and attaching separate components of a compression anastomosis device to the end of a hollow tissue section; and approximating the inserted first and second hollow tissue members using the device for approximating compression anastomosis device components such that the first and second collapsible members are interlocked together.

A novel tissue retaining device is also provided which is utilized to replace the use of conventional "purse string" suturing. The tissue retaining device includes a mating member having a receiving portion formed thereon, said receiving portion having an inner surface, and means for securing tissue to said mating member, said securing means comprising a ring having an outer surface dimensioned and configured for insertion into said receiving surface to compress tissue between said outer surface of said ring and an inner surface of said mating member receiving portion.

In one embodiment the ring is circular. Alternatively, the ring may have a uniform diameter. The tissue retaining ring has several advantages over conventional "purse string" suturing, for example, the ring is readily applied using the same instrument used to insert the other compression anastomosis device components. Therefore, less instrumentation is required in the operating room environment and less time is needed to prepare the tissue for the anastomoses.

BRIEF DESCRIPTION OF THE DRAWINGS

FIG. 2A is an exploded perspective view of the stent collapser, the stent finger assembly including the inner and outer fingers and the collapsing ring;

FIG. 2B is a partially cut-away side view illustrating the stent ring, inner stent fingers and outer stent fingers mounted together in a collapsed position;

FIG. 8 is a partial cross-sectional view taken along line 8—8 of FIG. 6 of the left side of the handle portion in the normal position ready for endoscopic deployment;

FIG. 14 is a partial perspective view of the distal end of the stent applicator device with the cutter blade extended;

FIG. 15 is a cross-sectional view taken along lines 15—15 of FIG. 13;

FIG. 17 is a view similar to FIG. 16, but shows the front trigger depressed whereby the snap ring is inserted into the stent assembly;

FIG. 18 is a horizontal cross-sectional view which shows the cutter blade in position ready to cut away excess tissue from the anastomotic site;

FIG. 19 is a cross-sectional view taken along the line 19—19 of FIG. 18 which shows the rotation of the cutting blade through the tissue;

FIG. 20 is a partial top plan view of the rear end of the handle member which shows the stent release toggle in the raised position;

FIG. 22 is a partial cross-sectional view taken along line 22—22 of FIG. 20 which shows part of the left-hand portion of the handle;

FIG. 23 is a partial view which shows the stent arbor at the distal end of the stent applicator instrument when the stent release toggle is in the raised position;

FIG. 35 is a partial plan view illustrating the triggers of the stent applicator handle in their pre-fired state;

FIG. 36 is a partial view of the distal end of the instrument with the elements positioned corresponding to the trigger positions of FIG. 35;

FIG. 37 is a view similar to FIG. 35 with the rear trigger depressed;

FIG. 38 is a view similar to FIG. 36, illustrating the expansion of the stent assembly upon depression of the rear trigger as shown in FIG. 37;

FIG. 39 is a view similar to FIGS. 35 and 37, which shows both the rear and the forward triggers depressed;

FIG. 40 is a view similar to FIGS. 36 and 38, which shows the snap ring being forced into the stent assembly by the forward trigger depression as shown in FIG. 39;

FIG. 41 is a view similar to FIG. 39, which shows the stent release toggle in the release position;

FIG. 42 is a view similar to FIG. 40, which shows the stent assembly released from the stent arbor after the stent release toggle is moved to the release position as shown in FIG. 41;

FIG. 63 is a diagrammatic view of the distal end of the stent closing instrument, which shows one finger pair in a closed position for insertion or removal in a cannula;

FIG. 64 is a diagrammatic view which shows the finger pair of FIG. 63 completely open corresponding to the toggle position in FIG. 60;

FIG. 65 is diagrammatic view which shows the finger pair of FIG. 63 in the clamped position, corresponding to the toggle position showing in FIG. 61;

FIG. 70 is an enlarged cross-sectional view taken along line 70—70 of FIG. 69 which shows the male and female axles coupled together.

DETAILED DESCRIPTION OF THE PREFERRED EMBODIMENTS

I. GENERAL

Figure 1:
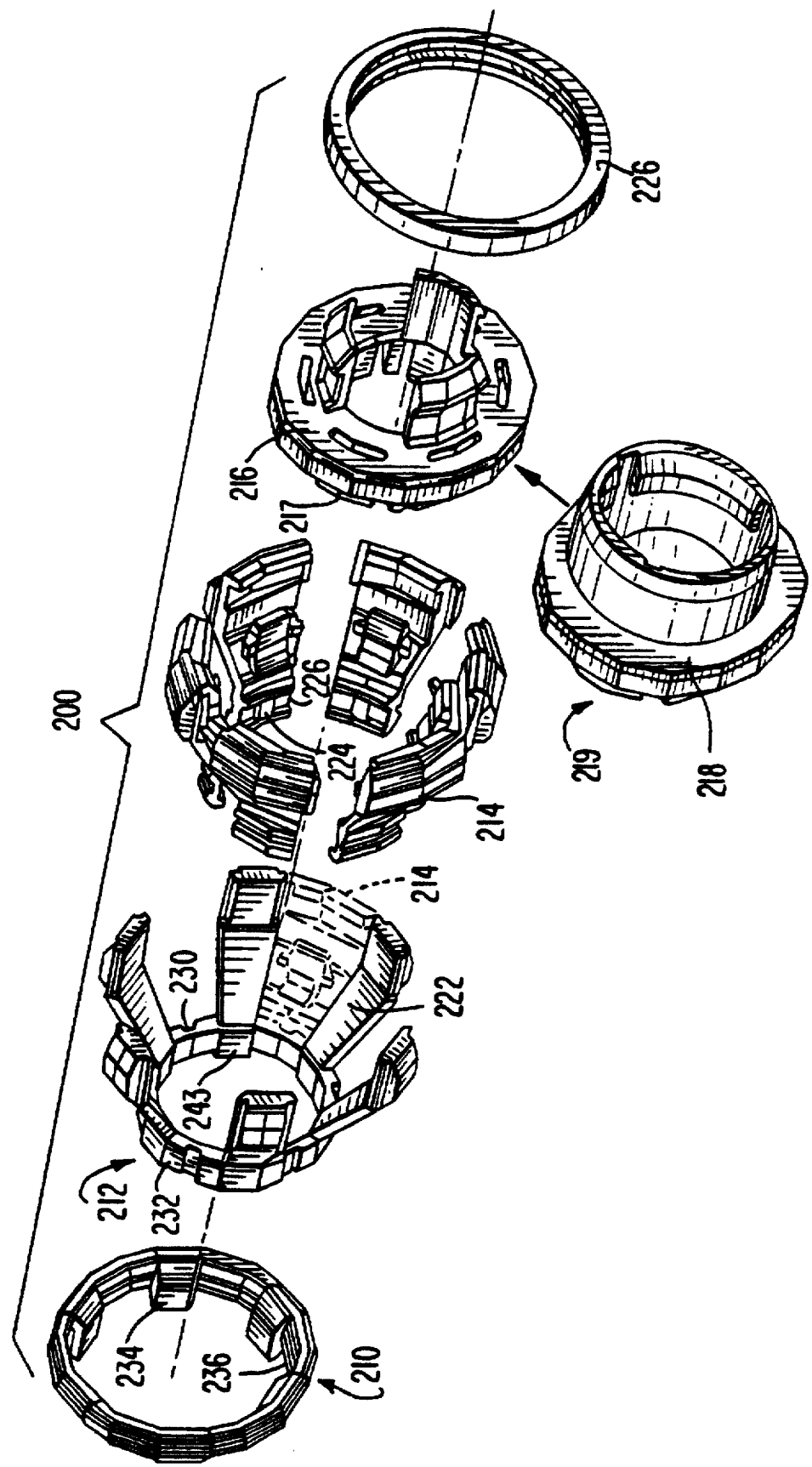
FIG. 1 is an exploded perspective view of the component parts of the stent ring, the inner stent fingers, the outer stent fingers, the male and female axles and the snap ring.

In general, the overall objective of the method and apparatus is to endoscopically place a collapsible anastomotic compressional stent device to achieve an end-to-end (or end-to-side, or side-to-side) anastomosis without resorting to open surgery or performing the anastomosis by rectal access. The invention includes three main parts: a collapsible stent assembly, a stent applicator instrument and a stent assembly closing device. The following is a short description of the parts of the stent assembly and the function or overall operation of the instruments used to place and join the stent.

Briefly, the collapsible stent assembly includes a number of component parts. A stent finger assembly including either a male or female axle member is assembled with a sub-assembly of inner stent fingers and outer stent fingers to form a male stent portion or female stent portion, respectively. The respective male and female stent portions are attached, by the insertion of a novel snap-ring, to the respective ends of a hollow organ to be joined. The snap-ring is utilized in lieu of conventional "purse-string" suturing which is typically applied to the end of each tissue section to be joined.

In order to achieve the placement of the stent portions, a novel applicator instrument has been developed which is inserted through the appropriately sized trocar cannula. The applicator instrument contains several mechanisms to effectively accomplish placement of the stent portions on the ends of the hollow organ to be anastomosed. As will be explained in detail, the applicator instrument is loaded with a snap-ring, the desired axle, i.e. male or female, and a collapsed stent finger assembly. The instrument is configured so that when either axle member is situated thereon they can be positioned to hold the stent finger assembly in the collapsed state during insertion through the trocar cannula.

Once the instrument has been inserted through the trocar cannula, one end of the hollow organ to be joined is pulled over the end of the instrument. When the instrument is partially inserted in the hollow organ, a unique mechanism is actuated which first causes the axle member to move away from the stent finger assembly until the axle is no longer engaging the stent finger assembly. Then in the same continued depression of the appropriate trigger, the mechanism causes the axle member to move toward the stent finger assembly entering it and causing the stent fingers to expand to their operational position. The axle member is configured to lock in place on the stent finger assembly.

When the axle member is locked in place a vacuum supply is turned on and the end of the tissue is pulled inwardly toward the central shaft of the instrument. A second trigger is pulled which forces a snap ring to pass over the tissue pulled toward vacuum holes on a shaft of the instrument. The snap ring locks into the end of the stent portion such that tissue is trapped between the snap ring and the base of the stent finger assembly. The procedure is repeated for the other end of the hollow organ to be anastomosed, except that a mating axle, either male or female which ever was not used for the first side, is used. When both male and female stent portions have been placed, the mating portions of the respective axle members are exposed on the end of the respective hollow sections ready to be joined.

In order to join the respective ends of the hollow organ, a unique closing device has been developed. The closing device includes two pairs of gripping fingers. One pair is attached to a wrist mechanism so that they can be moved toward and away from the other pair. One end section of the hollow organ to be joined is grasped between the first pair of fingers and the other end is grasped between the second pair of fingers. A trigger is pulled which activates a mechanism that closes the wrist and causes the pair of fingers attached to the wrist to move toward the other pair of fingers. The axle members mate and the anastomosis is complete.

The detailed description is divided into several sections to describe the structure and the desired movements produced thereby of the different apparatus of the present invention and a method for using those apparatus. Those sections include the stent assembly, stent assembly applicator and the stent assembly closing device. Each of these sections will be further sub-divided into sections describing the structure, operation and use of the various components. Also a kit containing the necessary instrumentation for performing an endoscopic placement of a collapsible anastomotic compression device is described.

The various apparatus components will be described throughout the following sections using the following numbering convention: components forming part of the stent assembly will be designated by reference numerals beginning with the number 200, components forming part of the stent applicator will be labeled with reference numerals beginning with 400 or 500 and components relating to the stent closing device will be labeled with reference numerals beginning with 600.

II. THE COLLAPSIBLE STENT ASSEMBLY

Referring initially to FIG. 1, the various components of a compression device for the anastomosis of hollow organs such as a collapsible stent assembly, for example, stent 200, are shown therein in exploded perspective view. Stent 200 is particularly adapted for endoscopic placement within an open end of a hollow organ. Except where noted otherwise, the materials utilized in the components of the collapsible stent generally include such biocompatible materials as polypropylene or urethane. The various components of the stent assembly may also be made from materials which are either partially or totally bioabsorbable, e.g. polylactide, polyglycolide, polydioxanone homopolymers, co-polymers or blends thereof.

The different components which make up stent 200 include clamping means, such as stent ring 210, inner stent finger member 212, outer stent fingers 214, male axle 216 (or alternatively female axle 218) and a tissue retaining member such as an annular ring or snap ring 220. To achieve an anastomosis, a first collapsible member or stent half, e.g., male stent portion 221 (FIG. 50), is constructed using male axle 216 in association with the remaining non-axle stent components set forth above and is inserted in one side of the hollow organ to be anastomosed. Another collapsible member or stent half, e.g., female stent portion 223 (FIG. 50), is constructed using female axle 218 in association with the remaining non-axle stent components set forth above and is inserted into the other hollow section to be anastomosed. The details of the procedures involved in placing the stent half portions in the respective hollow organ sections and then joining the stent-tissue complexes together will be described in the following sections.

PREPARATION OF THE STENT FINGER SUB-ASSEMBLIES

FIGS. 2A–5 illustrate the pre-assembly steps and collapsing procedure for forming a stent finger sub-assembly that can be employed with either male or female stent portions 221 and 223, respectively. The pre-assembly involves stent ring 210, inner stent finger member 212 and outer stent fingers 214. As shown in phantom lines in FIG. 1, outer stent fingers 214 are fitted on inner stent finger member 212 between inner stent fingers 222, such that raised portions 224 and channels 226 formed on the inner surface of lower end portions 228 fit in groove 230 and around crown 232, respectively. Once outer stent fingers 214 are in place around inner stent finger member 212, clamping means, such as an annular ring, for example, stent ring 210 is slid over crown 232 such that tab portions 234 of stent ring 210 over crown 232 such that tab portions 234 of stent ring 210 are aligned with inner fingers 222. Outer stent fingers 214 are further held in place between inner stent finger member 212 and stent ring 210 by means of rib portions 236 formed on the inner surface of stent ring 210, between tabs 234. Moreover, rib portions 236 are seated in channels 238 formed on the outer surface of lower end portion 228 of outer stent fingers 214.

The assembled stent fingers and stent ring are inserted in a specially developed compressing device such as stent collapser 240 of FIG. 2A. Stent finger assembly 242 is placed in stent collapser body 244 such that inner stent fingers 222 are aligned with stepped partitions 246. Stent collapser ring 248 is placed over stent collapser body 244 and stent finger assembly 242 such that posts 250 are aligned with cut-outs 252 and the top portion of outer stent fingers 214. Stent collapser ring 248 is depressed, as shown by FIG. 2B, so that posts 250 enter cut-outs 252 and force stent finger assembly 242 downward so that step partitions 246 urge inner stent fingers 222 inward.

Figure 3:
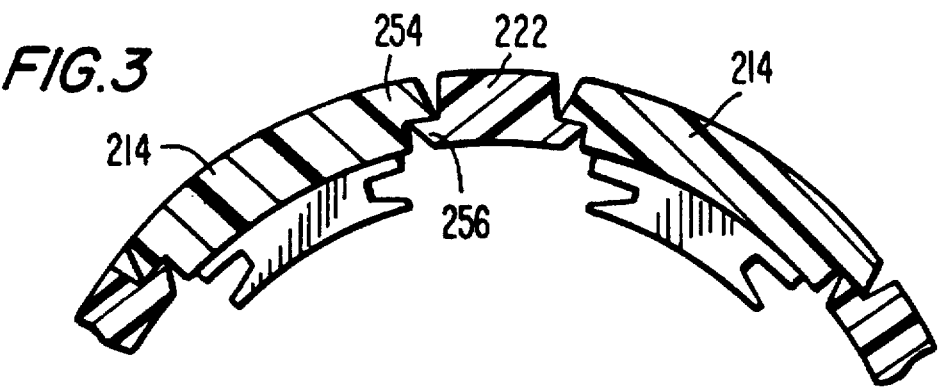
FIG. 3 is a vertical cross-section view of the top portions of the inner and outer stent fingers with the fingers in a pre-collapsed position.
Figure 4:
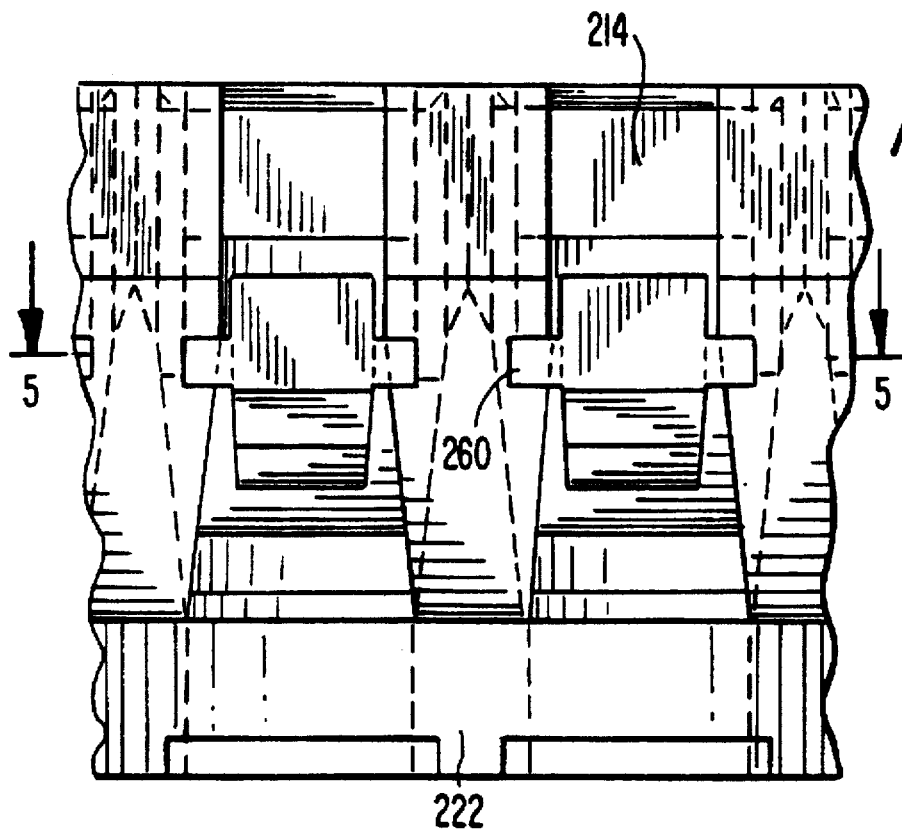
FIG. 4 is a partially cut-away side view of the inner surfaces of the inner and outer stent fingers in a collapsed position.
Figure 5:
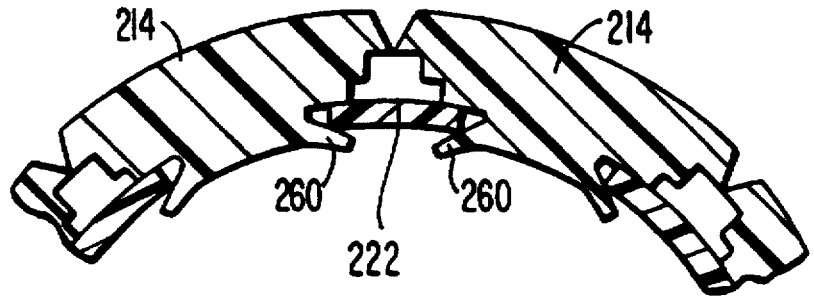
FIG. 5 is a cross-sectional view taken along line 5—5 of FIG. 4.

The relationship of inner stent fingers 222 and outer stent fingers 214 is best shown in FIGS. 3–5. In the cross-sectional top view of FIG. 3 the stent fingers are shown in a pre-collapsed state With inner stent fingers 222 situated adjacent outer stent fingers 214 in an opposing fashion whereby extended portion 254 of outer stent finger 214 is biased against extended portion 256 of inner stent finger 222. Upon collapsing of stent finger assembly 242, as shown in FIGS. 4 and 5, inner stent fingers 222 are urged inwardly by step partitions 246, FIG. 2A, and outer fingers 214 are urged closer to one another due to the reduced diameter of lower portion 258 of the inner surface of stent collapser body 244. Inner stent fingers 222 enter behind holding means such as tabs 260 disposed along the inner surface of outer stent fingers 214. Alternatively, other holding means may be provided such as latching members or the like. Stent finger assembly 242, now in a collapsed state and still held in stent collapser body 244, is ready for insertion onto the stent applicator device, described in the next section. This stent finger assembly can be used with the male stent portion 221 or female stent portion 223.

III. STENT APPLICATOR DEVICE

A. GENERAL

To place male stent portion 221 and female stent portion 223 in the respective portions of hollow organs to be joined together to form an anastomosis, a unique endoscopic instrument has been developed. One embodiment of that instrument is illustrated in the perspective view of FIG. 6 as stent applicator instrument 400. This section will first describe the various components making up the handle portion and endoscopic section of stent applicator instrument 400, as illustrated in FIGS. 7–11 and 12–15, respectively. Next, a description of the operation of the instrument's control elements will be presented, as illustrated in FIGS. 16–23. Then, the various steps to prepare the instrument for use will be described with reference to FIGS. 24–34. Next, the use of stent applicator instrument 400 will be described with reference to FIGS. 35–50. Finally, steps will be described, as are shown in FIGS. 51–54, for procedures where the instrument is to be re-used.

Figure 6:
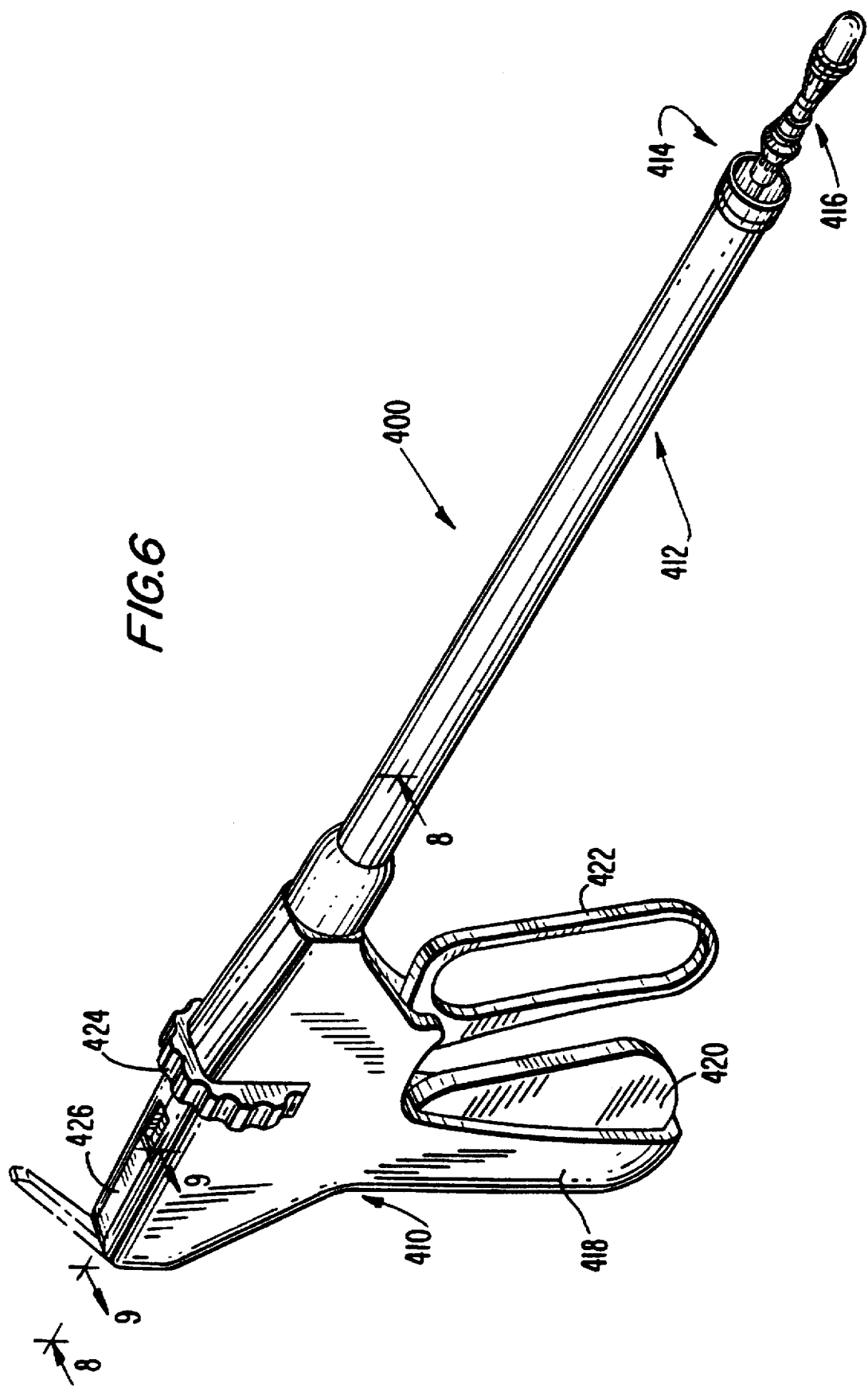
FIG. 6 is an overall perspective view of the stent applicator instrument.

As shown in FIG. 6, stent applicator instrument 400 includes handle portion 410 and endoscopic section 412. Endoscopic section 412 has a distal end portion 414 which provides a carrying and placement mechanism 416 adapted to place either male stent portion 221 or female stent portion 223 in the end of a hollow organ to be anastomosed. Handle portion 410 of stent applicator instrument 400 includes manual grip 418, a first trigger or first actuating means, such as axle lever 420, a second trigger or second actuating means, such as snap ring insertion lever 422, a knurled finger operative dial such as tissue cutter dial 424 and a finger operative lever, such as stent release toggle 426.

Figure 16:
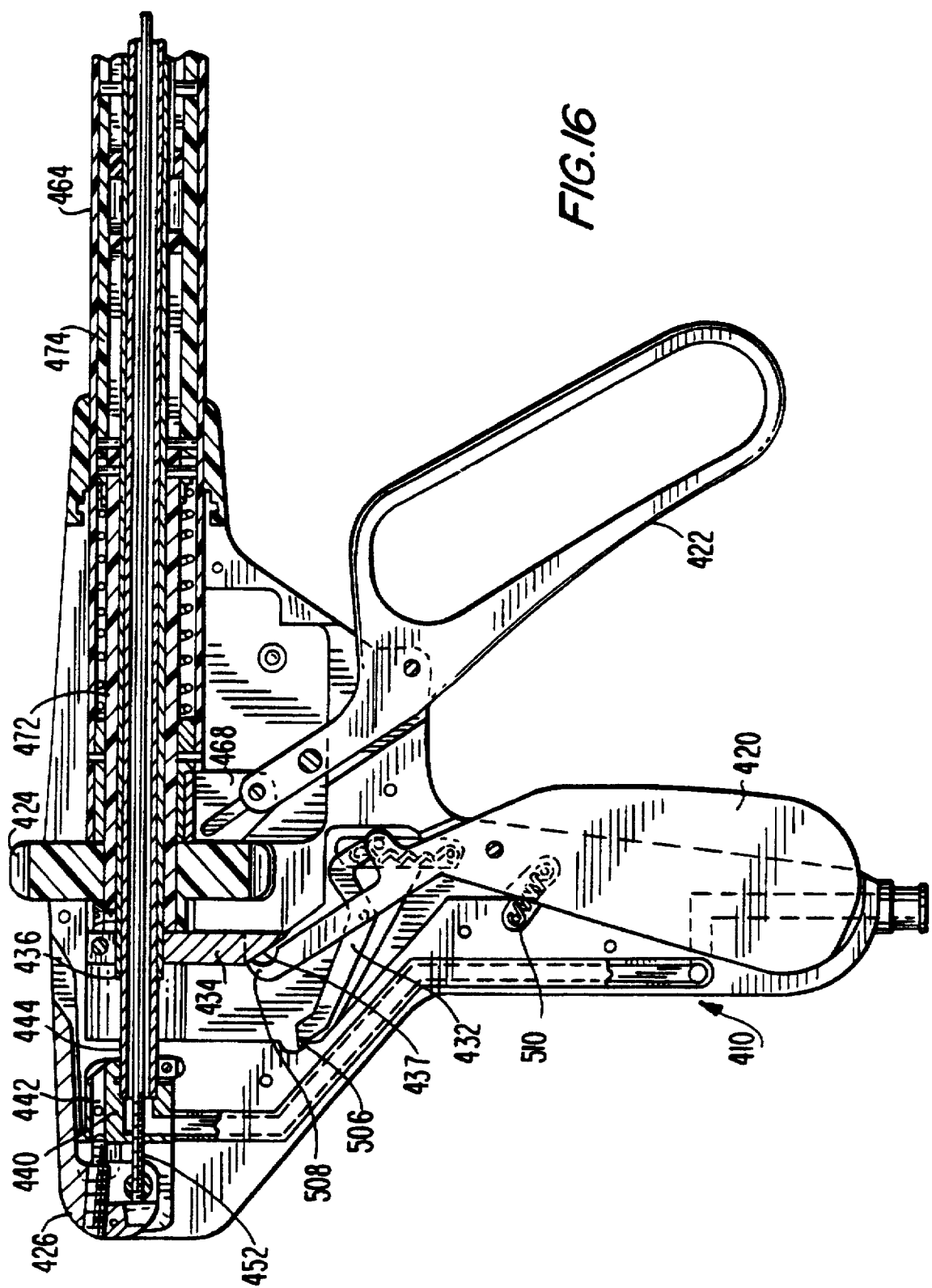
FIG. 16 is a view similar to FIG. 8, but shows the rear trigger depressed.

Referring temporarily to FIG. 16 in conjunction with FIG. 14, axle lever 420 pivots toward manual grip 418 to first move axle holder 496 located at distal end portion 414 of the instrument, a short distance, of approximately 1 mm to approximately 3 mm in a proximal direction. With continued depression of axle lever 420 toward manual grip 418, assembling means, such as axle holder 496 then moves distally to force axle 216 or 218, loaded thereon, into stent finger assembly 242 carried on support means, such as stent arbor 500 which is also located in distal end portion 414. Therefore, a single complete depression of axle lever 420 towards manual grip 418 causes axle holder 496 to initially move in a proximal direction, a short distance, and then to move in a distal direction. Axle holder 496 and stent arbor 500 will be described in further detail later in this section.

Referring once again to FIG. 6, snap ring insertion lever 422 pivots toward manual grip 418 to urge driving means, such as snap ring tube 464 (FIG. 12) carrying snap ring 220 shown in FIG. 1, in a distal direction. This locks the tissue of one end of the hollow organ to be anastomosed in the stent finger assembly 242 with snap ring 220. The use of the snap ring 220 eliminates the need for what is conventionally known as "purse-string" sutures to close the ends of the hollow organ prior to forming the anastomosis.

Tissue cutter dial 424 rotates clockwise to rotate tissue cutter 494 and to advance the tissue cutter 494 distally. Tissue cutter dial 424 is further rotated clockwise to complete excision of excess tissue around the newly inserted stent half portion. Stent release toggle 426 pivots upward (shown in phantom) away from handle portion 410 to release the inserted stent half portion from stent applicator instrument 400. Each of these structural components and their operation will now be described in detail.

B. THE HANDLE PORTION

Figure 7:
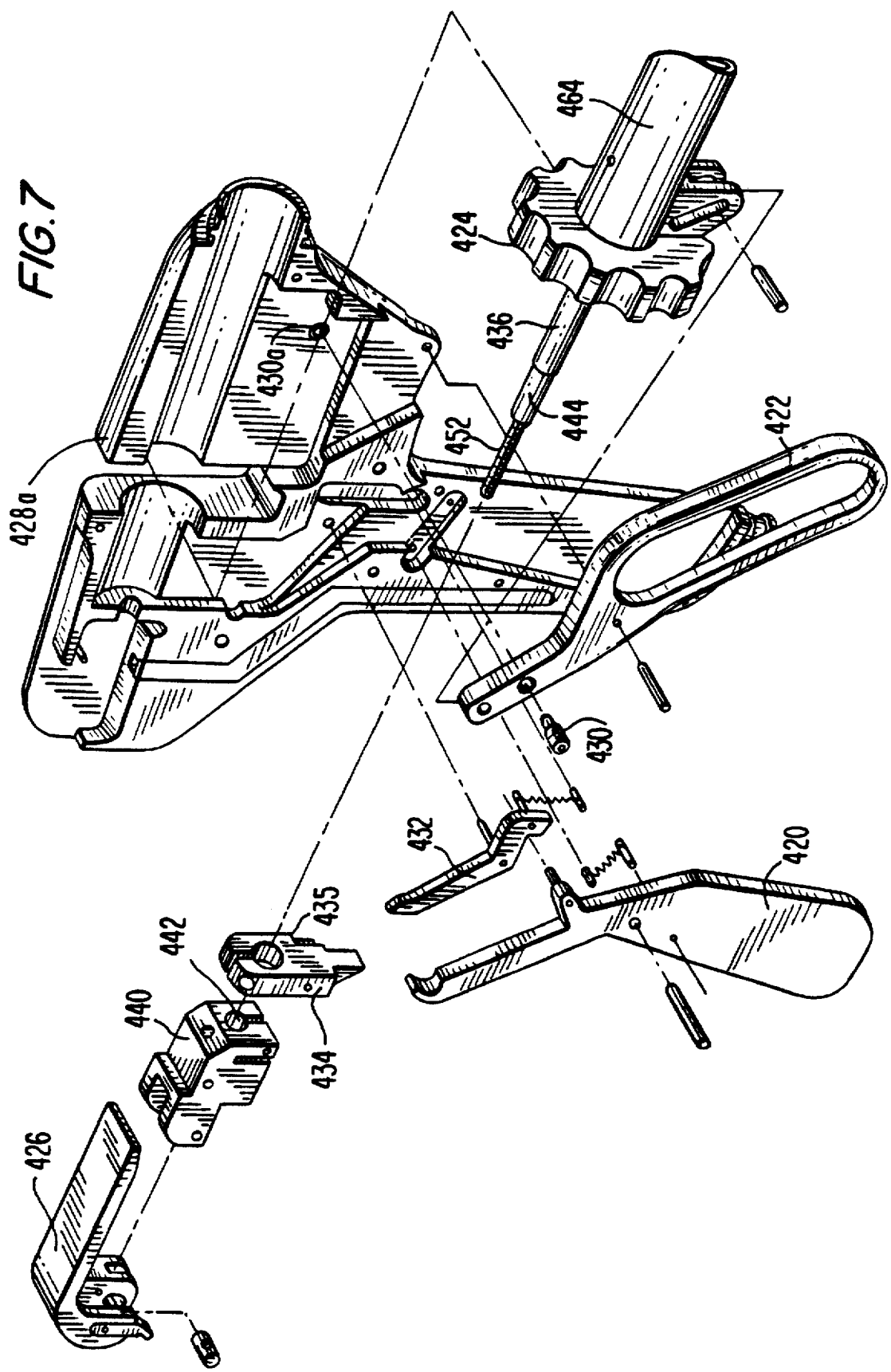
FIG. 7 is an exploded perspective view of the stent applicator handle showing the various component parts separated.

In FIG. 7, handle portion 410 is shown in exploded perspective view with one half-section of the cover removed for purposes of illustrating various internal components. The purpose of handle portion 410 is to provide controlled movement of carrying and placement mechanism 416 (FIG. 6) at distal end portion 414. Manual grip 418 includes split half-sections 428a and 428b (FIGS. 7, 8, 9, 10 and 21). The split half-sections comprise an outer housing for handle portion 410 which is typically formed of a polycarbonate material. Half-sections 428a and 428b may be attached by welding, adhesives, etc.

Snap ring insertion lever 422 is pivotably mounted in the distal end portion of manual grip 418. In a preferred embodiment, lockout means are provided to prevent snap ring insertion lever 422 from further movement once the lever has been pulled its full travel distance thereby inserting the snap ring in position. Any suitable lockout means may be utilized, such as, for example, spring loaded pin 430 cooperating with receiving bore 430a formed in split half-section 428a of handle portion 410. The lockout means helps assure the user that the snap ring, once inserted, will not be pulled out of the stent accidently.

Once fired, snap ring insertion lever 422 remains locked in place for the completion of the procedure. If it is desired that the instrument be reused, spring loaded pin 430 can be reset by inserting an appropriately adapted pin or the like into the bore formed in split half-section 428a, thereby freeing snap ring insertion lever 422 to return to its initial position. Alternatively, a reset button (not shown) or the like may be permanently mounted in the receiving bore formed in split half-section 428a. Snap ring insertion lever 422 is operatively attached to an outer tube of endoscopic section 412 which is spring loaded to bias the outer tube in a proximal direction as will be described in further detail in the following section.

Axle lever 420 is pivotably mounted in handle portion 410 in reverse pivotal cooperation with axle release lever 432, which is also pivotably mounted in handle portion 410. Axle tube yoke 434 is securely mounted to axle tube 436 such that upon depression of axle lever 420, axle release lever 432 pivots such that a top portion thereof moves toward the proximal end of stent applicator instrument 400. Axle release lever 432 contacts axle tube yoke 434 and urges it toward the proximal end of stent applicator instrument 400 for a distance of approximately 1 mm to approximately 3 mm. Then, upon further depression of axle lever 420, extended portion 438 of axle lever 420 contacts axle tube yoke 434 and urges it distally. The function and purpose of this mechanism will be better understood from the description presented in the section entitled OPERATION.

Air fitting 440 is mounted in a recessed portion formed in handle half sections 428a and 428b such that gas port 442 is in gaseous communication with arbor tube 444 and gas port 446 (shown in FIG. 8). Gas port 446 is in gaseous communication with passageway 448 formed in handle half section 428a, as shown in FIG. 8. Passageway 448 in turn communicates with vacuum supply connector 450. Stent release toggle 426 is operatively connected to push rod 452, which is slidably disposed within arbor tube 444, which in turn is slidably disposed within axle tube 436. These different components and their functional relationships will be described in greater detail in the following section. Tissue cutter dial 424 is rotatably mounted to the proximal end of endoscopic section 412 and its structural and functional relationships will also be discussed in greater detail in the following section. Tissue cutter dial 424 extends from housing half sections 428a and 428b through cut-outs formed therein, respectively.

Figure 10:
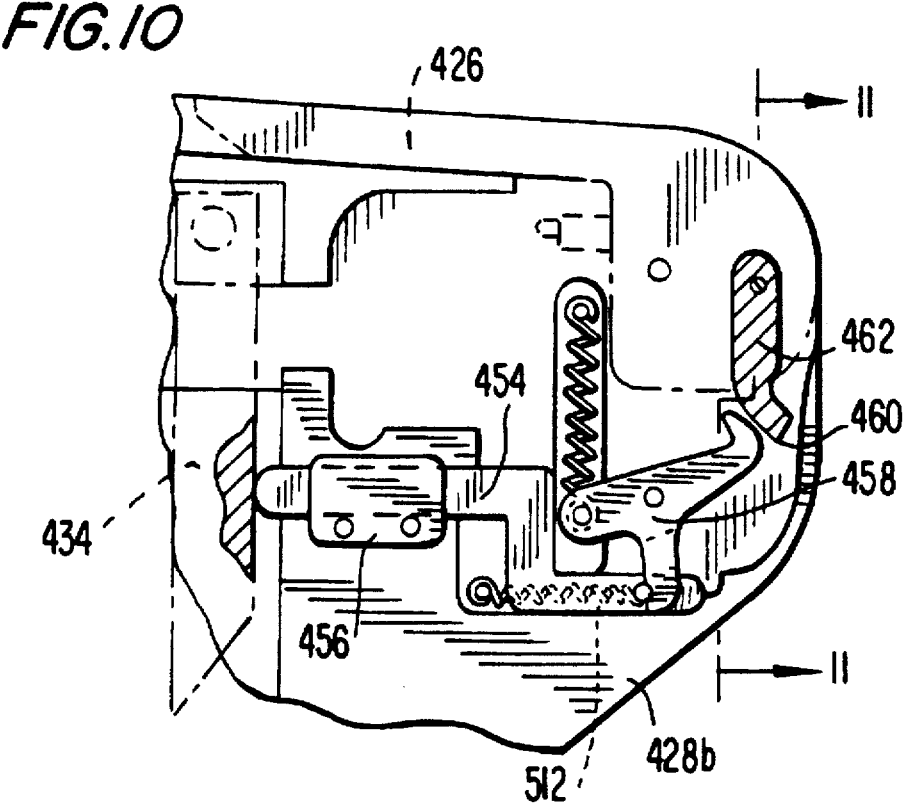
FIG. 10 is a fragmentary cross-sectional view taken along line 9—9 of FIG. 6.
Figure 11:
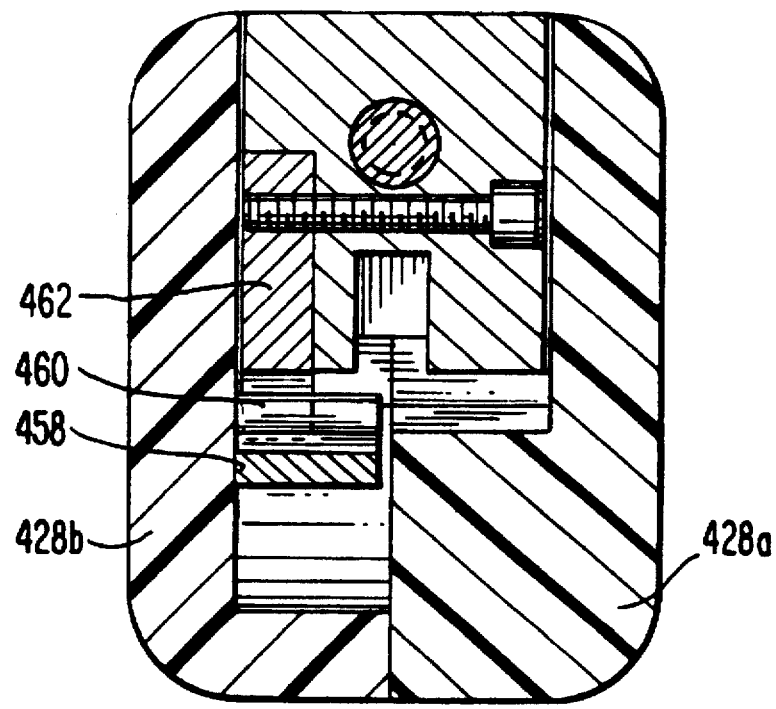
FIG. 11 is a cross-sectional view along line 11—11 of FIG. 10.
Figure 9:
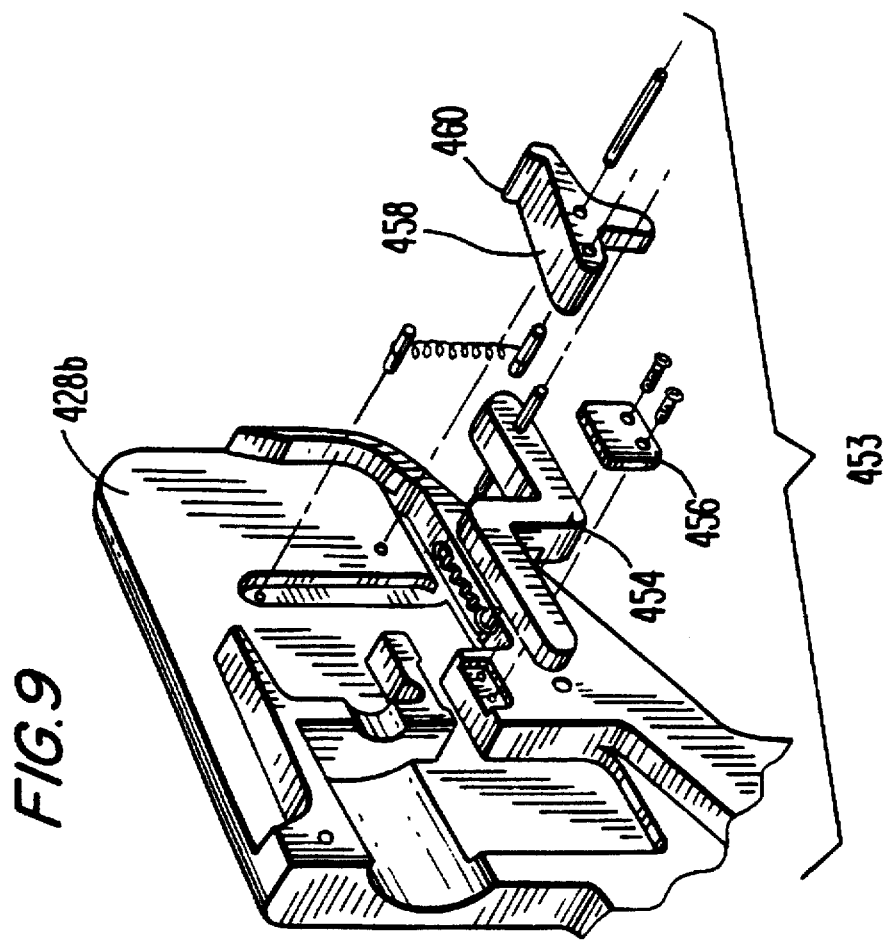
FIG. 9 is an exploded partial view of the stent release lockout mechanism.

FIGS. 9, 10 and 11 illustrate a lock-out feature for preventing premature release of the stent from the stent arbor. The components of lock-out mechanism 453 are best shown in the exploded partial view of FIG. 9. Striker bar 454 is spring loaded and biased toward axle tube yoke 434 such that striker bar 454 abuts axle tube yoke 434 when yoke 434 is in a prefired position. Cover plate 456 serves to hold striker bar 454 in a recess formed in handle half section 428b. Striker bar 454 is operatively associated with pivoting lock-out member 458 which is spring loaded in housing half section 428b such that extended barrier portion 460 is urged downwardly away from extension member 462 (FIG. 21) of stent toggle release lever 426. The lock-out prevents stent toggle lever 426 from being raised to release the stent from the stent arbor unless axle tube yoke 434 has been moved distally away from striker bar 454.

C. THE ENDOSCOPIC SECTION

Figure 12:
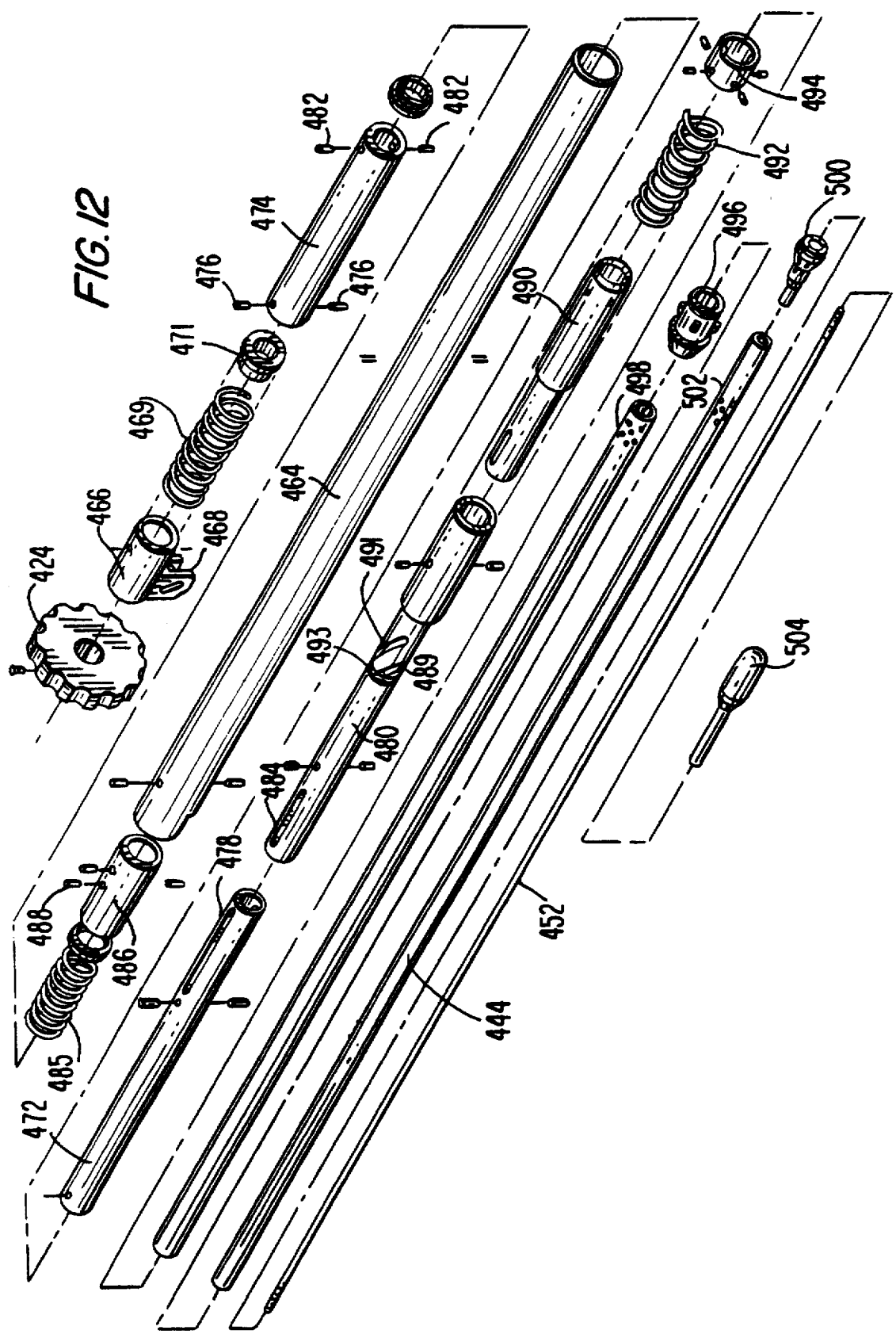
FIG. 12 is an exploded perspective view of the endoscopic section of the stent applicator with the various components separated.
Figure 13:
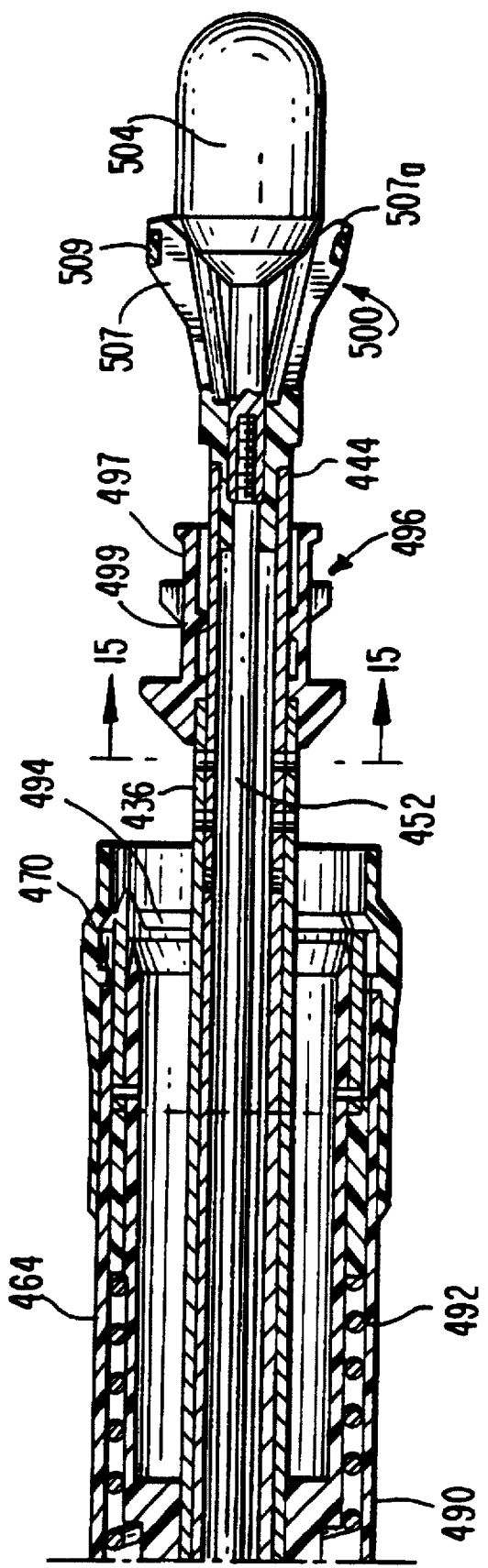
FIG. 13 is a horizontal cross-sectional view of the distal end of the stent applicator instrument which shows the stent arbor, the axle holder and the cutter blade retracted within the body of the instrument.

Referring now to FIG. 12, endoscopic section 412 is shown in exploded view, with parts separated, for convenience of illustration and includes numerous concentric components which make up several sub-assemblies for performing the various functions of stent applicator instrument 400. The first of the sub-assemblies to be described facilitates insertion of a tissue retaining member such as snap ring 220 when snap ring insertion lever 422 is pulled to its proximal-most position. Snap ring tube 464 is secured at a proximal end to drive bushing 466 having drive yoke 468 securely fastened thereto. Drive yoke 468 is operatively connected to snap ring insertion lever 422 of handle portion 410 such that when snap ring insertion lever 422 is pulled by the operator towards manual grip 418, snap ring tube 464 is urged distally away from handle portion 410. Spring 469, which rests on bearing 471, biases drive bushing 466 and thus snap ring tube 464 toward the proximal end of stent applicator instrument 400. Snap ring holder 470 is mounted at the distal end of snap ring tube 464, as best illustrated in FIGS. 13 and 14.

In a preferred embodiment, snap ring holder 470 consists of a thin wall tube having narrow fingers, such as fingers 471 shown in FIG. 14, cut in a distal end thereof. Fingers 471 have narrow lip 473 which mates with a groove formed in snap ring 220. The fingers are designed to be normally flexed inward, i.e. in a disengaged position with respect to snap ring 220. In a loaded position, the fingers are biased outward by an object such as a cutter blade which will be described in further detail later in this section. In the loaded position the cutter blade or other object pushes out on fingers 471 which engage and hold snap ring 220 in place on snap ring holder 470. When it is desired to release snap ring 220, the cutter blade or other biasing object is retracted so that is moves behind snap ring holder 470 allowing the fingers to flex inward thus releasing snap ring 220 from the distal end of snap ring tube 464.

Referring again to FIG. 12, a tissue cutting sub-assembly is shown positioned within snap ring tube 464, which also serves as a housing for endoscopic section 412. The tissue cutting sub-assembly comprises drive shaft 472 secured at a proximal end to tissue cutter dial 424 and secured to handle split half-sections 428a and 428b such that drive shaft 472 is fixed relative to handle portion 410. Drive shaft 472 is slidably connected to coupling member 474, for example, by way of pins 476 frictionally fit in bores formed near the proximal end of coupler member 474 sliding in diametrically opposed slots 478 formed on the outer surface of drive shaft 472. This causes the tissue cutting sub-assembly to move along with snap ring tube 464 upon depression of snap ring insertion lever 422.

At the distal end of coupling member 474, cutter cam 480 is mounted in a similar fashion as drive shaft 472, i.e. pins 482 being frictionally fit in bores formed near the distal end of coupling member 474 and fitting within slots 484 formed on cutter cam 480 near a proximal end thereof. Spring 485 biases cutter cam 480 distally. Cam follower 486 is secured to snap ring tube 464 and cooperates with cutter cam 480 by way of camming pin 488 fitting into a cam track having two helical camming slots, shorter camming slot 489 corresponding to a ready-for-use position and longer camming slot 491 corresponding to a stored position. The operation of these camming slots will be described in further detail in the following section. Cutter cartridge 490 is slidably mounted within the distal end of cutter cam 480 and is biased by spring 492 distally away from cutter cam 480. Cutter ring 494 is securely mounted at the distal end of cutter cartridge 490.

Disposed within the tissue cutting assembly is an axle holder and insertion sub-assembly wherein axle tube 436 has axle tube yoke 434 securely attached to a proximal end (FIG. 7) and axle holder 496 securely attached to a distal end. Axle holder 496 has fingers 497, best shown in FIG. 14, fabricated to be normally in a collapsed state. Protruding portions 499 (FIGS. 13 and 18) are disposed along the inner surface of each finger 497 and are biased against arbor tube 444 pushing fingers 497 radially outward. This structural configuration provides for holding the appropriate axle member on axle holder 496. When axle holder 496 is advanced distally, protruding portions 499 fall into gap 501 (FIG. 14) formed between the distal end of arbor tube 444 and stent arbor 500.

Vacuum holes 498 are formed through axle tube 436, adjacent to axle holder 496, which is best illustrated in FIG. 14. Referring again to FIG. 12, arbor tube 444 is positioned within axle tube 436 and is securely mounted at the proximal end in air fitting 440 (FIG. 7). Stent arbor 500 is securely attached to a distal end of arbor tube 444. Vacuum holes 502 are formed near the distal end of arbor tube 444 and are preferably aligned with vacuum holes 498 of axle tube 436, as shown in cross-section in FIG. 15.

Slidably positioned within arbor tube 444 is push rod 452 which is operatively connected to stent release toggle 426 (FIG. 7) at a proximal end and has spreader member 504 attached to a distal end. Spreader member 504 is adapted to spread open fingers 507 formed on stent arbor 500 which are normally biased radially inward by elastomeric ring 509.

D. OPERATION

The operation of the control members of stent applicator instrument 400 will now be described with reference to FIGS. 16–23.

Depression by the operator on axle lever 420 as shown in FIG. 16, causes axle release lever 432 to pivot such that top portion 506 swings toward the distal portion of handle portion 410. Axle release lever 432 thereby makes sliding contact with axle tube yoke 434 (FIG. 8) urging it in a proximal direction for a distance of approximately 1 mm to approximately 3 mm. This motion initially pulls axle tube 436 in a proximal direction and consequently axle holder 496 and whichever axle member is mounted thereon, either male axle 216 or female axle 218, also in a proximal direction. Upon further depression of axle lever 420 axle release lever 432 loses contact with axle tube yoke 434 by passing into a void within handle portion 410 formed by a cut-out on the axle tube yoke 434, as illustrated by a phantom line on axle tube yoke 434 in FIG. 16 and designated 435 in FIG. 7. This cut-out can be varied to alter the length of proximal travel of axle tube 436. After still further depression of axle lever 420, upper portion 508 of axle lever 420 makes contact with axle tube yoke 434 along angled surface 437, extending therefrom, thereby urging distally mounted axle holder 496 (FIG. 13) in a distal direction. Upon complete depression, axle lever 420 remains in the fully depressed position due to the spring biasing provided by spring 510.

Snap ring insertion lever 422 is squeezed by the operator, as shown in FIG. 17, urging drive yoke 468 in a distal direction thereby driving snap ring tube 464 into the stent assembly. Tissue cutter dial 424 is rotated clockwise to advance cutter cartridge 490 and cutter ring 494 distally into position to cut excess tissue away from the anastomotic site, as shown in FIGS. 18 and 19. In an alternative embodiment, tissue cutter dial 424 may be eliminated and the excess tissue left remaining.

Figure 21:
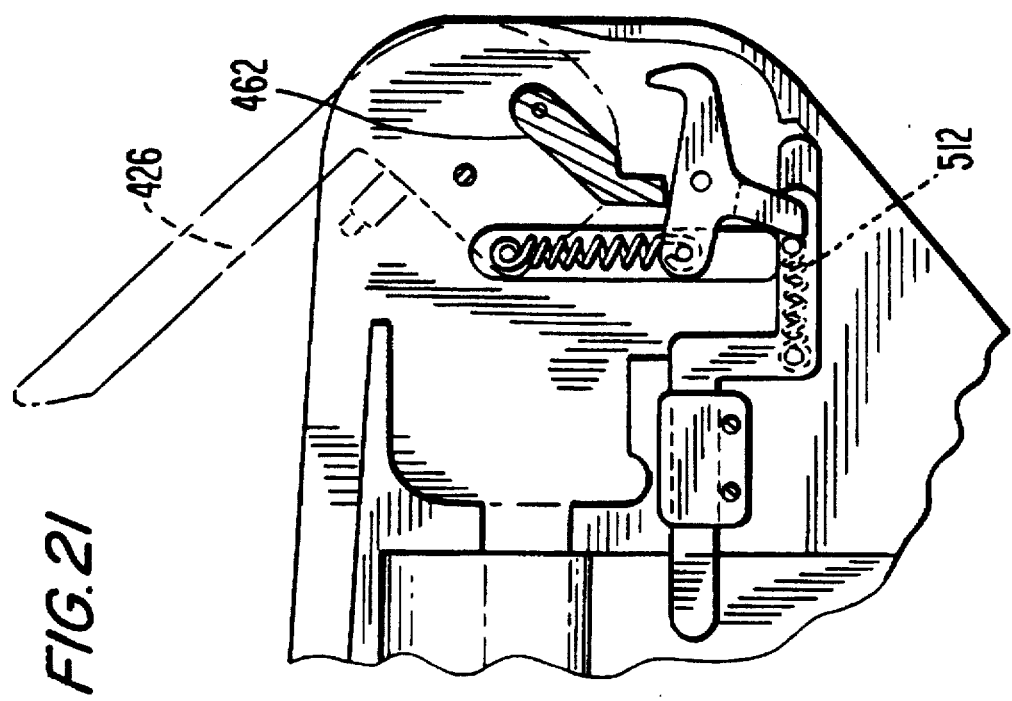
FIG. 21 is a partial cross-sectional view taken along line 21—21 of FIG. 20 which shows part of the right-hand portion of the handle.

The operation of stent release toggle 426 is illustrated in FIGS. 9 and 20–23. Once axle tube yoke 434 is moved distally by axle lever 420, striker bar 454 is urged distally by spring 512 thereby lowering pivotably mounting lock-out member 458 and providing sufficient clearance for extension member 462 to pass without contact therewith (FIG. 21). Stent release toggle 426 can then be raised, as shown in FIG. 22, to move spreader 504 (FIG. 23) distally away from stent arbor 500, thereby releasing the stent assembly (not shown in FIG. 23) from stent arbor 500.

E. PREPARATION FOR USE

Figure 24:
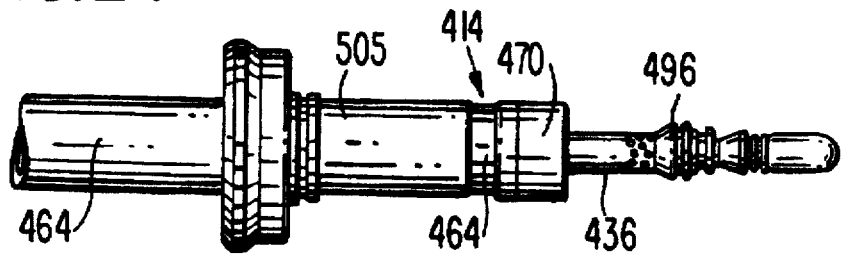
FIGS. 24-26 show some of the steps of preparing the stent applicator instrument for use.
Figure 25:
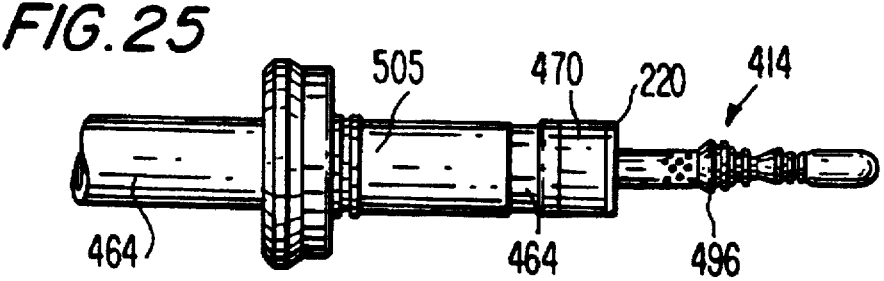

In FIGS. 24–34, several preparatory steps are illustrated which are preferably performed immediately prior to beginning the surgical procedure. In one preferred embodiment, stent applicator instrument 400 is configured such that minimal positioning of components is necessary, when taken from any packaging which may be provided with the instrument. For example, snap ring insertion lever 422 is preset, i.e. in the pre-fired state, axle lever 420 is in the fully depressed position (as shown in FIG. 16) with axle holder 496 in the forward position, as shown in FIGS. 24 and 25. Cutter ring 494 is in the fully proximal or reset position (FIG. 13) with camming pin 488 (FIG. 12) located in the closed end of longer helical camming slot 491 provided on cutter cam 480, to allow for retraction thereof, proximal of snap ring holder 470 (FIG. 13) and within snap ring tube 464. Stent release toggle 426 is in the raised or open position.

Figure 52:
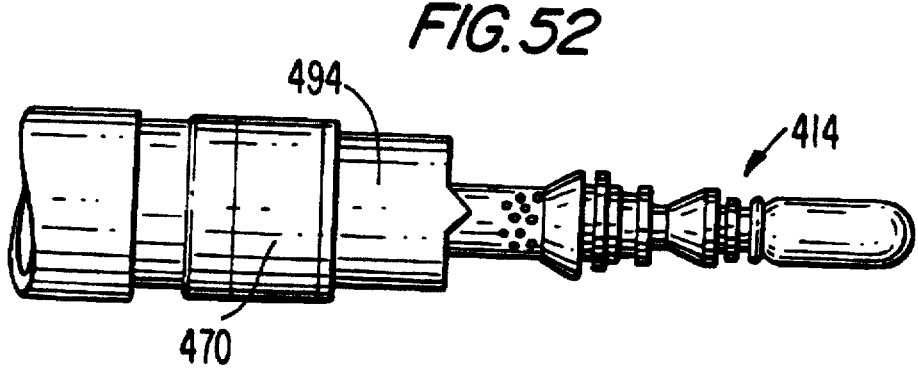
Figure 53:
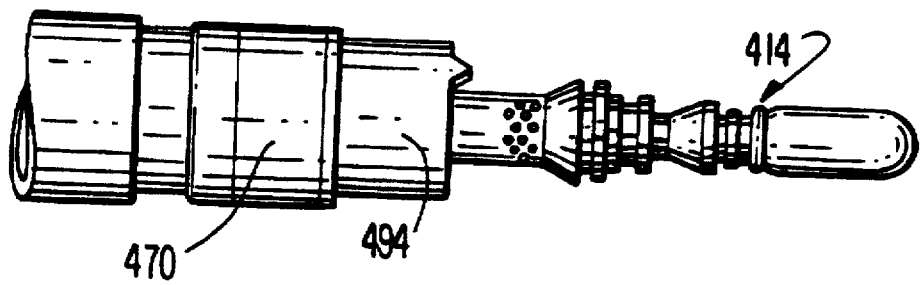
Figure 54:
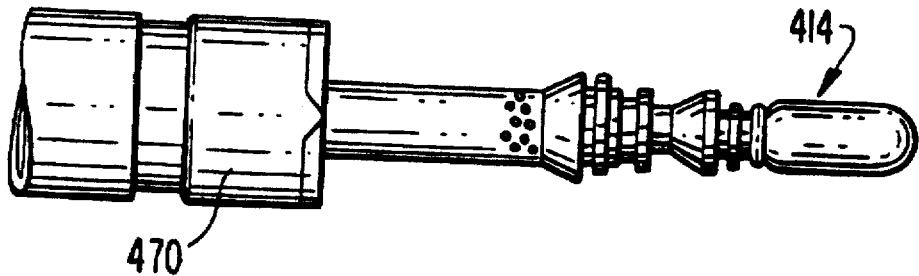

Although not critical, the preferred order of preparing stent applicator instrument 400 for use involves the following steps. Trocar adapter 505 is passed over distal end 414 of stent applicator instrument 400 as shown in FIG. 24. Snap ring 220 is inserted on snap ring holder 470 as shown in FIG. 25. Referring temporarily to FIGS. 52–54, cutter ring 494 is advanced to its distal-most position by rotating tissue cutter dial 424 (FIG. 1) clockwise until cutter ring rotates without further distal travel (not shown). From distal end 414 looking proximally, cutter ring 494 is then pulled distally, either by hand or with any suitable grasping instrument and rotated counter-clockwise (facing blade 494a), approximately one-quarter turn, as shown in the progression from FIG. 52 to FIG. 53, to switch the alignment of camming pin 488 from longer camming slot 491 (FIG. 12) where it was originally, to align camming pin 488 with shorter camming slot 489 (FIG. 12). Tissue cutter dial 424 is then rotated counterclockwise so that shorter camming slot 489 receives camming pin 488 (FIG. 12). Upon further counterclockwise rotation of tissue cutter dial 424, cutter ring 494 comes to rest in its loaded position, which due to the shorter length of helical camming slot 489 is at a more distal location than the stored position such that cutter ring 494 pushes radially outward on snap ring holder 470. In this position, cutter ring 494 urges fingers 471 of snap ring holder 470 radially outward to help hold snap ring 220 in place when same is loaded in place.

Cutter ring 494 is now ready for use, such that upon clockwise rotation of tissue cutter dial 424, cutter ring 494 rotates and moves distally as camming pin 488 guides cutter cam 480 until camming pin emerges from shorter camming slot 489 and enters annular groove 493. Then, upon further clockwise rotation of tissue cutter dial 424, cutter ring 494 rotates at a fixed position relative to the distal end of stent applicator instrument 400.

Figure 26:
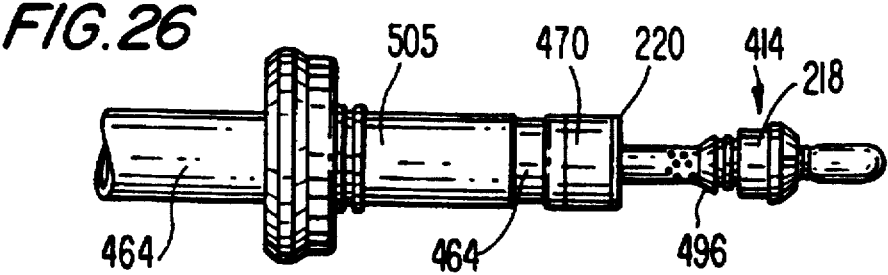
Figure 29:
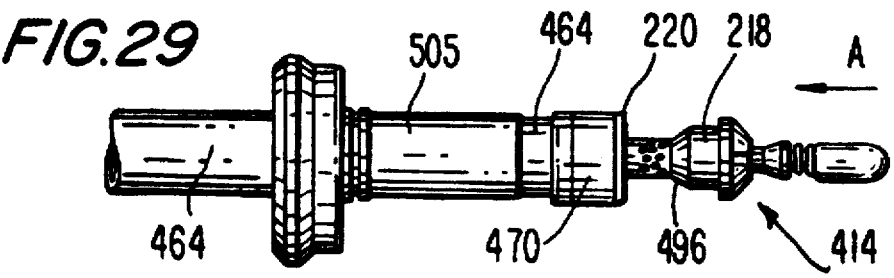
FIG. 29-31 are views which show steps, subsequent to those of FIGS. 24-26, in preparing the stent applicator instrument for use.
Figure 27:
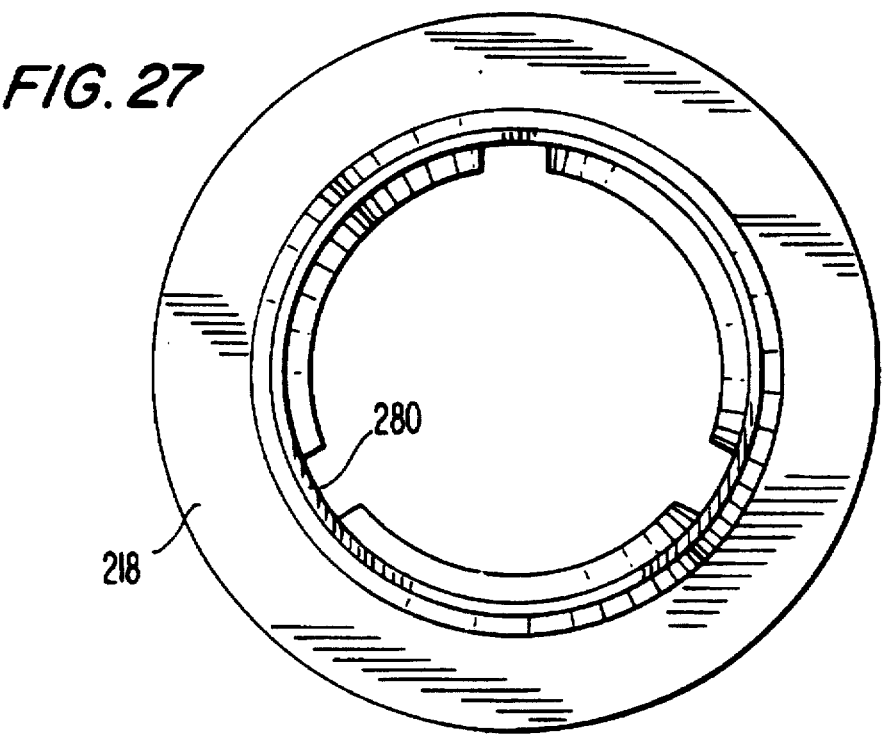
FIG. 27 is an end plan view of the female axle of the stent assembly.
Figure 28:
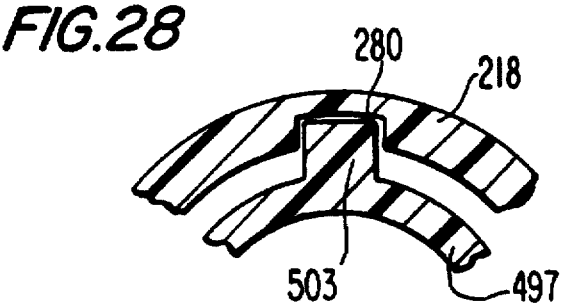
FIG. 28 is a partial cross-sectional view showing the keying of the stent axle to the axle holder on the stent applicator instrument.

Either male or female axle 216 or 218, respectively, is attached to axle holder 496 (female axle 218 is shown in FIG. 26). The axle is attached such that slots 280 formed along its inner surface, as shown on female axle 218 in FIG. 27, are aligned with keys 503 formed on fingers 497 of axle holder 496, as shown in FIG. 28. The mounted axle is then pushed proximally, as is indicated by arrow A in FIG. 29, so that axle holder 496 and axle tube 436 move proximally. This resets axle lever 420 to the position of FIG. 29 and retains either male axle 216 or female axle 218 (as shown in FIG. 18) on axle holder 496. Retention occurs because, as axle holder 496 moves proximally, protruding portions 499 (FIG. 13) initially slide in gap 501 (FIG. 14) and with further proximal movement then cam over the distal end of arbor tube 444. This urges fingers 497 radially outward such that keys 503 bias against slots 495 thereby applying sufficient radial pressure to retain either axle member on axle holder 496.

Figure 32:
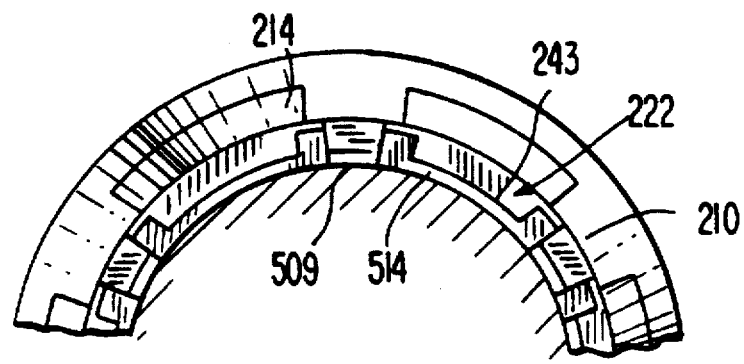
FIG. 32 is a partial end view of the distal end of the stent applicator which shows a stent assembly locked onto the stent arbor.
Figure 30:
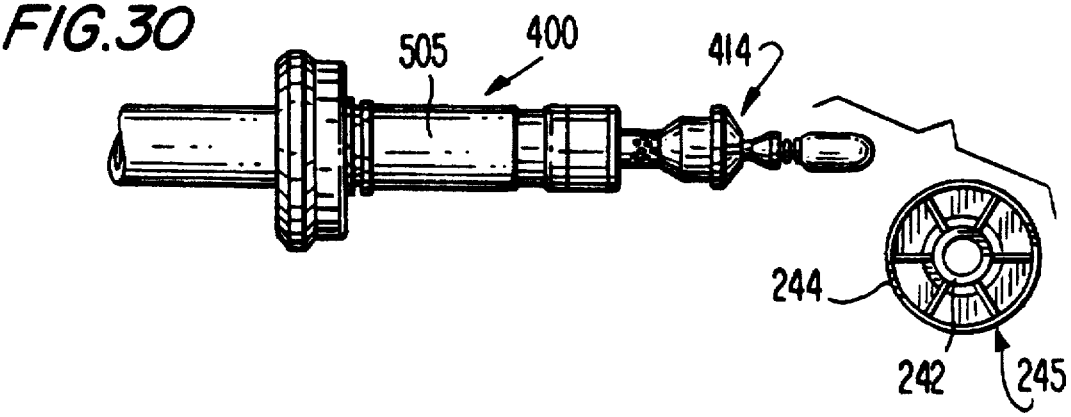
Figure 31:
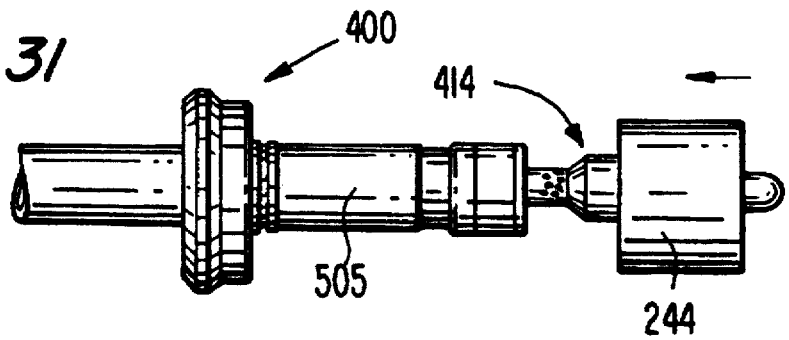
Figure 33:
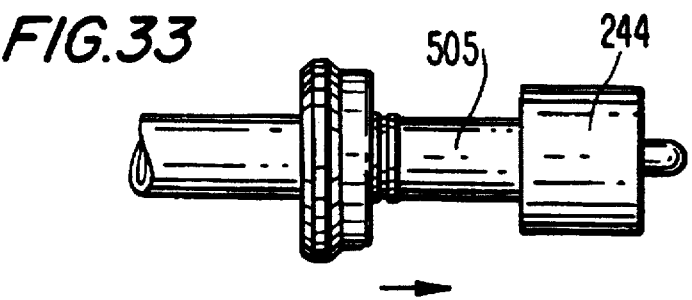
FIG. 33 and 34 are views which show steps, subsequent to those of FIGS. 29-31, in preparing the stent applicator instrument for use.

FIGS. 30–34 illustrate the steps of placing stent finger assembly 242 (FIG. 2A) on stent arbor 500. Sub-assembly 245 consists of stent collapser body 244 containing stent finger assembly 242, already in the collapsed position, as shown by FIG. 30 and described in the section entitled PREPARATION OF THE STENT FINGER SUB-ASSEMBLIES. Sub-assembly 245 is passed over distal end 414 of stent applicator instrument 400, FIG. 31, such that keys 243 on distal end 211 of stent finger assembly 242 align with channels 514 formed on distal end 516 (FIG. 14) of fingers 507 of stent arbor 500, as shown in FIG. 32. In this position, the collapsed inner stent fingers 222 will seat under the distal end 217 or 219 (FIG. 1) of either male axle 216 or female axle 218, respectively, whichever is loaded on axle holder 496. Stent finger assembly 242 will remain held in the collapsed state, until the axle 216 or 218 is moved proximally to release the inner stent fingers. The stent finger assembly remains in the collapsed configuration until axle 216 or 218 is moved proximally because (i) the axle 216 or 218 holds inner stent fingers 222 and (ii) inner stent fingers 222 pull radially inward on holding means, such as tabs 260 of outer stent fingers 214 (FIG. 5).

Stent finger assembly 242 is then locked on stent arbor 500. Stent release toggle 426 is lowered pulling spreader 504 proximally within the open end of stent arbor 500. Fingers 507, normally biased radially inward by elastomeric ring 509, are urged radially outward so that channels 514 of stent arbor 500 engage keys 243 of inner stent finger member 212 to hold stent finger assembly 242 on stent arbor 500, as shown in FIG. 32. Trocar adapter 505 is pushed distally until it contacts and pushes stent collapser body 244 off the distal end of stent applicator instrument 400, as shown in the progression from FIG. 33 to FIG. 34. Thus, stent applicator instrument 400 is now ready to apply one half-stent portion, i.e. male stent portion 221 (FIG. 50) or female stent portion 223 (FIG. 50) containing either a male or female axle, respectively, to the open end of one of the hollow sections to be joined.

F. USE OF STENT APPLICATOR INSTRUMENT

Figure 34:
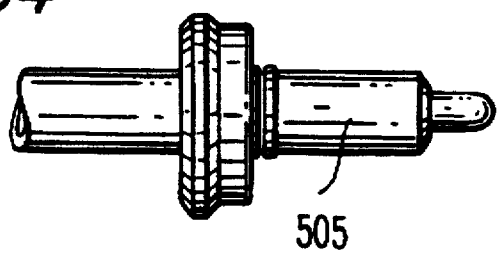
Figure 43:
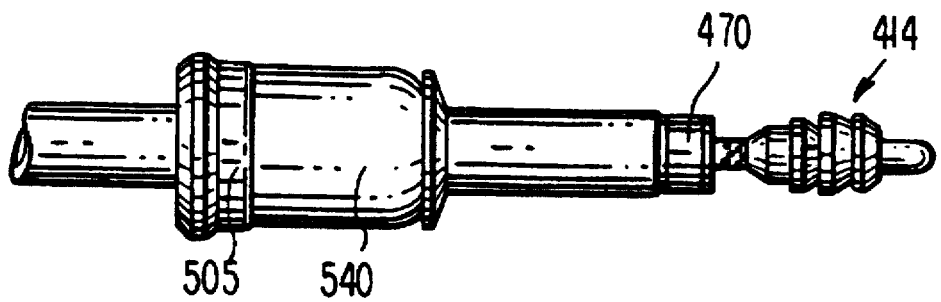
FIGS. 43-49 illustrate steps of attaching a stent assembly to one side of a hollow organ to be joined during an anastomosis.

Stent applicator instrument 400 will now be described in use. FIGS. 35–42 show the various handle control portion positions at proximal end 410 and the corresponding actions occurring at distal end 414 of instrument 400. FIGS. 43–50 show the actions occurring at the distal end of instrument 400 when applying a stent half-portion to one end of a hollow tissue section to be joined. Stent applicator instrument 400 is first prepared for use as described in the above sub-section bearing that title. It is then inserted into trocar adapter 505 and then into the appropriate trocar, such as trocar 540, at the laparoscopic surgical site. At this point, distal end 414 of instrument 400 is preferably arranged as shown in FIG. 34, with the handle portion appearing as illustrated in FIG. 35. Once trocar adapter 505 reaches the proximal portion of trocar 540, instrument 400 is further inserted so that trocar adapter 505 remains stationary and the stent finger assembly 242 as well as axle 216 or 218 emerge therefrom, as shown in FIGS. 36 and 43.

Figure 44:
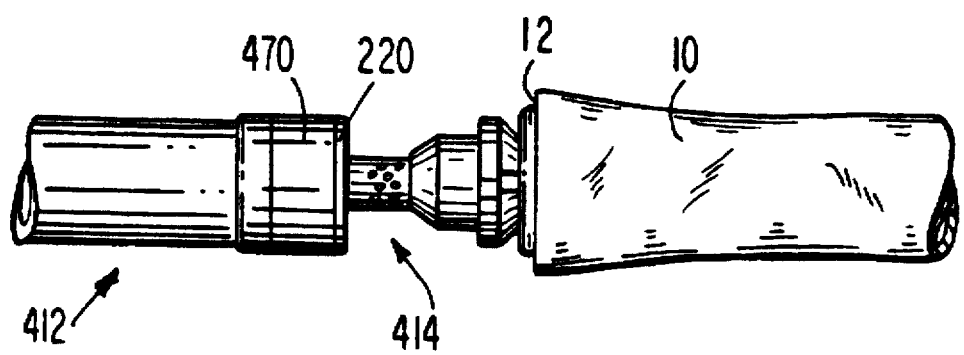
Figure 45:
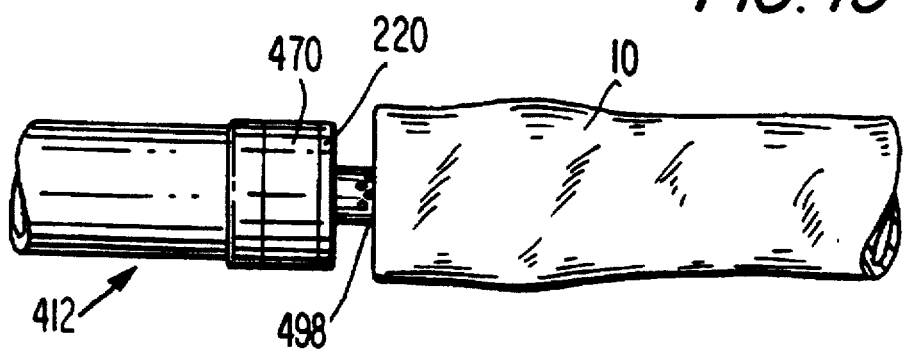

Distal end 414 of stent applicator instrument 400 is then inserted in the open end of one of hollow sections 10 to be joined, as shown in FIG. 44. Preferably, endoscopic grasping instruments (not shown), known in the art, are inserted down other cannulas already in place and pull the open end 12 of the tissue over distal end 414 of instrument 400. Once the tissue is in position over vacuum holes 498, as shown in FIG. 45, axle lever 420 is squeezed to drive axle 218 (or 216) into stent finger assembly 242, as shown in FIGS. 37 and 38. As described in a previous section, upon squeezing axle lever 420, axle holder 496 first moves proximally a short distance of approximately 1 mm to approximately 3 mm, or any distance sufficient to allow inner stent fingers 222 to be released from axle 218 (or 216). Stent finger assembly 242 thereby expands and inner fingers 222 spread open slightly. Then, upon further squeezing of axle lever 420, axle holder 496 moves axle 218 (or 216) distally causing the axle to enter the proximal end of the stent finger assembly 242. When axle lever 420 is fully depressed, axle 218 (or 216) causes stent finger assembly 242 to expand to its full diameter which is approximately 2–4 mm greater than that of the cannula. Axle 218 (or 216) becomes latched in stent finger assembly 242 (FIGS. 18 and 38) by way of latching means, such as extended portions 218a and 218b of axle 218 (or extended portion 216a of axle 216, not shown) engaging locking means, such as recessed portions 214a and 214b of outer stent fingers 214, as shown in FIG. 18.

Figure 46:
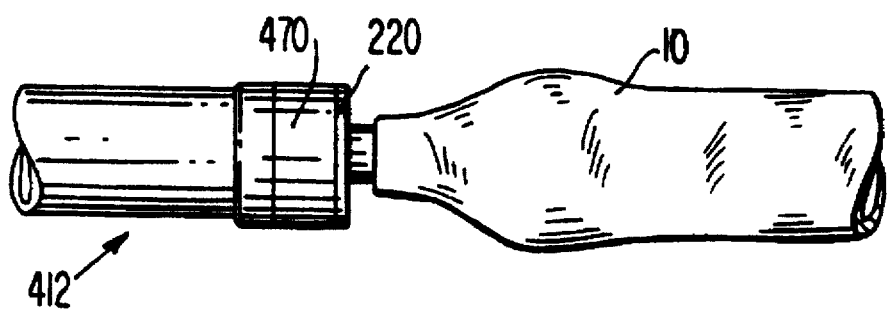
Figure 47:
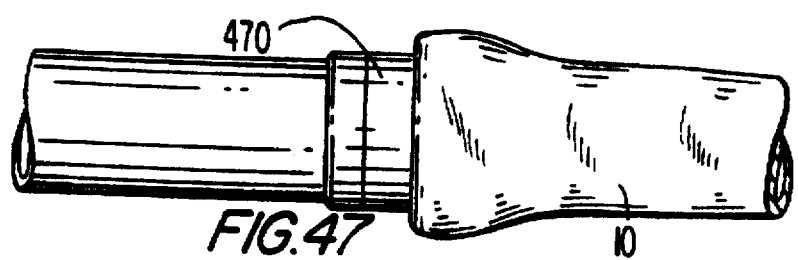
Figure 48:
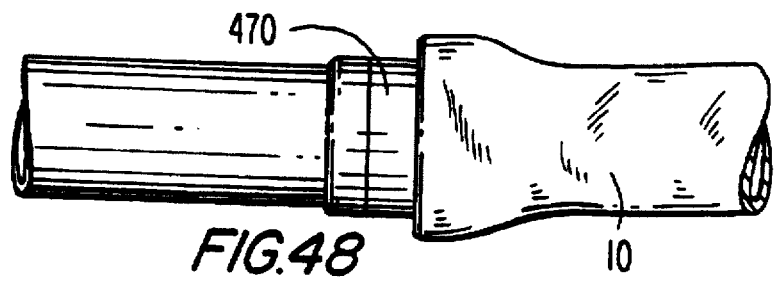

At this point, instead of tying a conventional "purse-string" suture to hold end 12 of hollow organ section 10 within the diameter of the compressional surfaces of the stent fingers (the proximal end 213 of stent finger assembly 242, as shown in FIG. 2A ), a vacuum source (not shown) is operatively connected to vacuum supply connector 450 (FIG. 8). Any suitable vacuum source may be used, such as commercially available units particularly adapted for use in surgical procedures. When the vacuum is switched on, end 12 of the hollow organ 10 is sucked radially inward, as shown in FIG. 46. Intentional vacuum leaks may be provided in axle holder 496 and stent arbor 500. These leaks allow the tissue to be pulled down onto axle 218 (or 216) and stent finger assembly 242, as well as at vacuum holes 498. By using the vacuum source to hold the end of the hollow organ in place, much time and effort on the part of the surgical team is saved.

The insertion of snap ring 220 will best be understood with reference to FIGS. 39, 40 and temporarily back to FIG. 18. With the vacuum source still turned on, snap ring insertion lever 422 (FIG. 39) is pulled to pass the snap ring holder 470 and snap ring 220 distally over end 12 of tissue held on vacuum holes 498 and 502. As snap ring 220 moves distally over the tissue it forces the tissue to fold over proximal end 213 (FIG. 2A) of stent finger assembly 242 by snap ring 220 and snap ring holder 470. As snap ring 220 continues to move distally it passes along camming surface 260 formed on the inside of outer stent fingers 214. This spreads the outer stent fingers sufficiently to allow snap ring 220 to enter into annular groove 262 formed along the inner surface of outer stent fingers 214. A portion of end 12 of tissue is thus retained between snap ring 220 and the inner surface of annular groove 262. The stent half-portion (consisting of the snap ring 220, stent finger assembly 242 and axle 216 or 218) is now securely attached to end 12 of the hollow tissue section.

Referring momentarily to FIGS. 18 and 19, once snap ring 220 is securely in place, the vacuum supply is turned off. Tissue cutter dial 444 (FIG. 6) is rotated clockwise for approximately three turns such that blade 494a of cutter ring 494 separates excess tissue from within the longitudinal through-passageway (i.e. lumen) of the stent half-portion. Tissue cutter dial 444 it is then rotated counterclockwise causing the longer slot 491 of the two helical camming slots 489, 491 to travel over camming pin 488 so that cutter ring 494 returns to its proximal-most or stored position.

Figure 49:
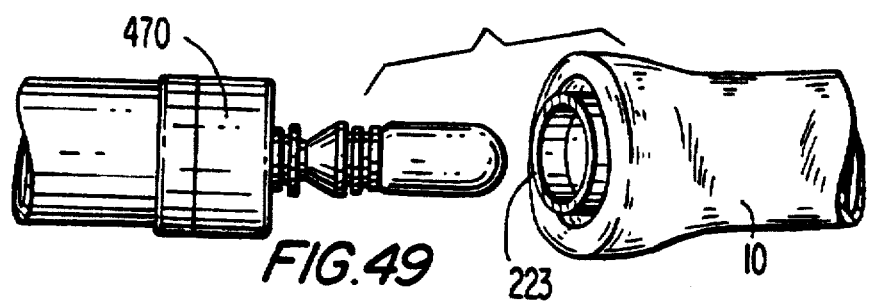
Figure 50:
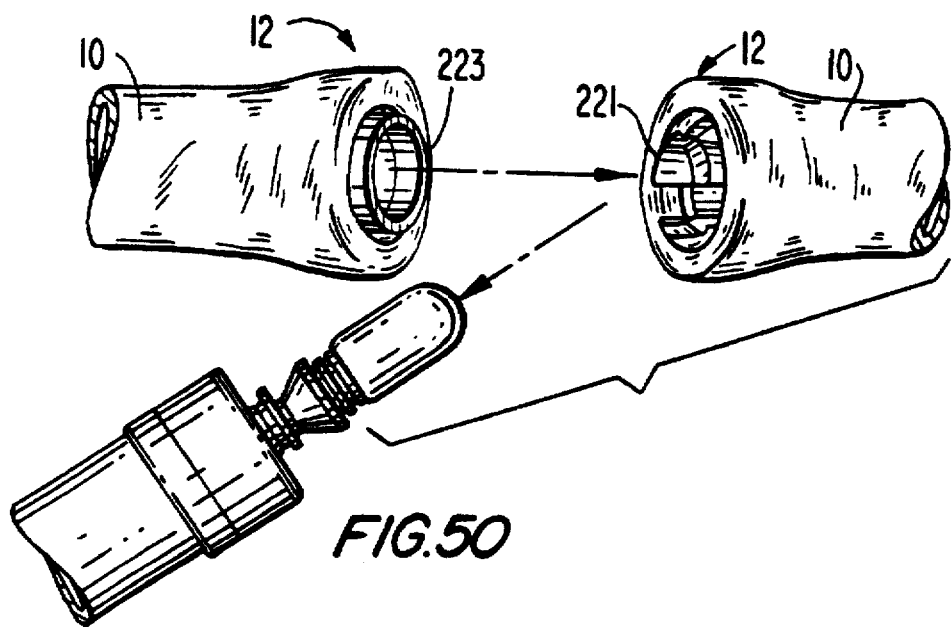
FIG. 50 illustrates the completed insertion of both male and female stent portions in the ends of the hollow tissue.

The newly formed tissue stent half-portion complex is released from stent applicator instrument 400 by raising stent release toggle 426, as shown in FIGS. 41, 42 and 49. The above procedure is then repeated to insert the mating stent half-portion in the other end section 12 of hollow organ 10 to be joined. Once completed the two ends 12, 12 are ready to be joined, as shown in FIG. 50. It is within the scope of the present invention for the distal end of stent applicator instrument 400 to be detachable from the handle portion so that a second distal end, ready-to-use, may be at the surgical site. However, stent applicator instrument 400 may be re-usable for the same instrument to place both stent half-portions in place. If the same instrument is used to place both stent half-portions, then some steps must be taken to reset the instrument and prepare it with the appropriate stent assembly components as described in the following section.

G. PREPARATION FOR RE-USE

Figure 51:
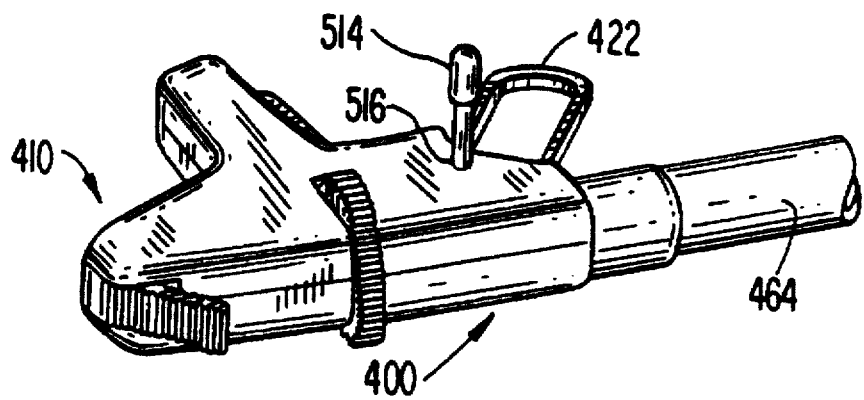
FIGS. 51-54 illustrate preparation steps required before reusing the instrument.

FIGS. 51–54 show the steps necessary to prepare stent applicator instrument 400 for re-use. Snap ring insertion lever 422 is released from the locked out position by inserting reset tool 514 into reset bore 516, as shown in FIG. 51, to compress the spring of spring loaded pin 430 (FIG. 7). Once the spring is compressed, the spring loading of snap ring tube 464 causes it to move proximally thereby pivoting snap ring insertion lever 422 back to the pre-fired position.

Cutter ring 494 is reset by rotating tissue cutter dial 424 clockwise until cutter ring 494 is fully extended, as shown in FIG. 52. This seats camming pin 488 in annular groove 493 of cutter cam 480 (FIG. 12). Facing the distal end of stent applicator instrument 400, cutter ring 494 is pulled distally and rotated clockwise (facing the blade 494a and looking proximally) approximately ⅛ of a turn, as shown in the progression from FIG. 52 to FIG. 53. This transfers camming control from the longer helical camming slot 491 to the shorter helical camming slot 489 for allowing the cutter ring to be placed in the snap ring holding position. The cutter ring is retracted by rotating tissue cutter dial 424 counterclockwise until it stops, i.e. until camming pin 488 seats in the closed end of shorter helical camming slot 489.

The cutter ring is at this point positioned just inside snap ring holder 470, as shown in FIG. 54. Stent applicator instrument 400 is now ready to be prepared for use according to the above section of the same title.

IV. STENT ASSEMBLY CLOSING DEVICE

A. GENERAL

To join male stent portion 221 and female stent portion 223, a unique closing device has been developed. The device is illustrated in perspective view at FIG. 55 as stent assembly closing device 600. Although the following description will focus on application of the instrument for joining male and female stent portions 221 and 223, respectively, clearly the instrument can be adapted for use in approximating other surgical implant device components or the like. Except where noted otherwise, the materials utilized in the components of the device generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) may also be utilized. However, equivalent alternative materials will readily come to the mind of those skilled in the art.

Stent assembly closing device 600 includes handle portion 610 and endoscopic section 612 having at distal end portion 614 approximating means, such as wrist and finger mechanism 616. Included in wrist and finger mechanism 616 are wrist 618 having a first pair of grasping means, such as fingers 620, which are pivotably operable between at least an open position and a closed position, attached thereto. A second pair of grasping means, such as fingers 622 are also provided which are also pivotably operable between at least an open position and a closed position (FIGS. 63–65). In the closed position, fingers 626 and 622 are able to be inserted through a cannula for access to the surgical site. In a preferred embodiment at least one intermediate locking position is provided so that fingers 620 and 622 may be locked in a predetermined degree of closure position during usage of the device.

Figure 55:
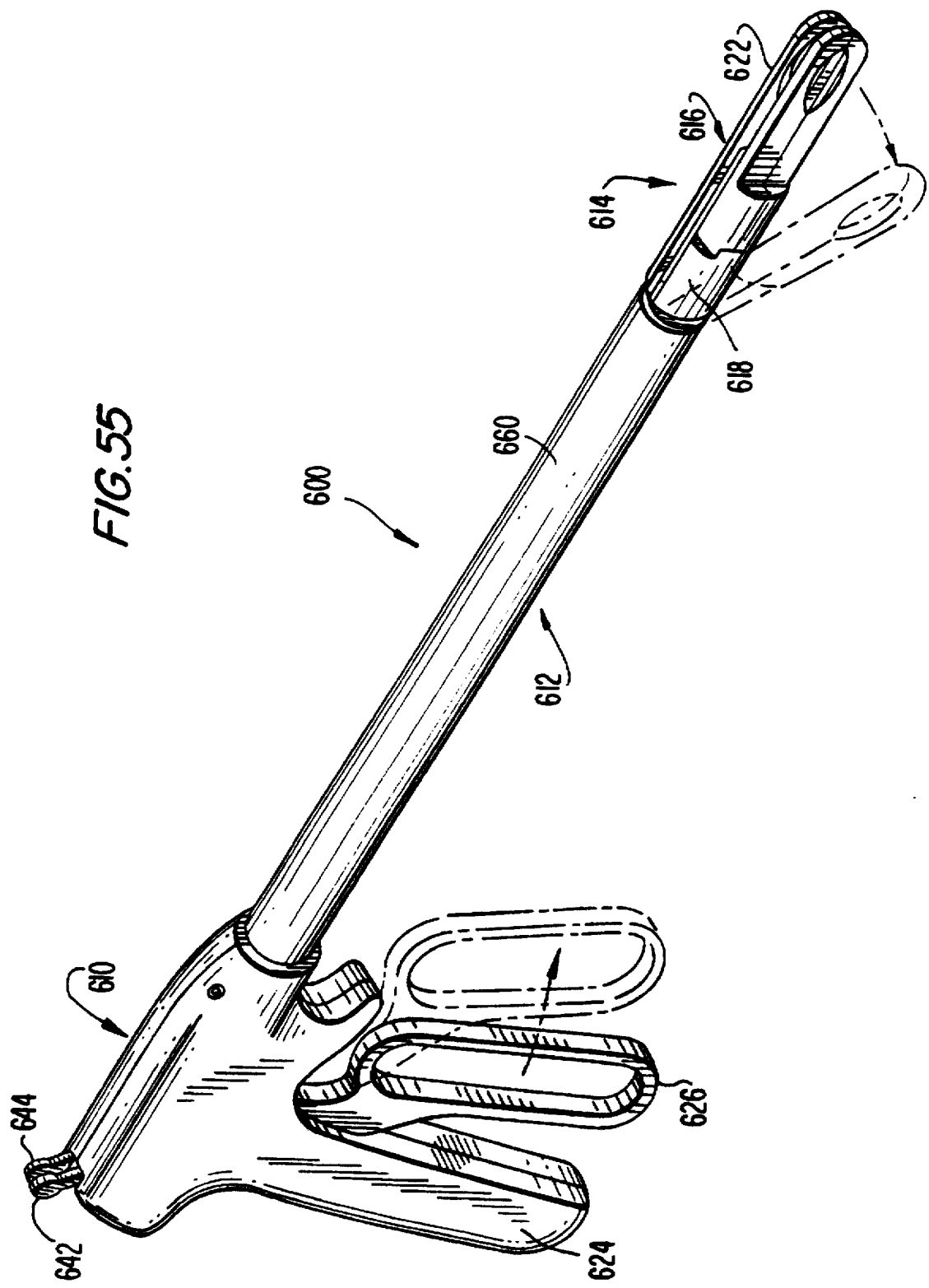
FIG. 55 is a perspective view of the stent assembly closure device with a portion shown in phantom lines to illustrate a range of movement of the wrist portion.

Generally, wrist 618 will selectively pivot up to about 30° with respect to a longitudinal axis extending centrally through endoscopic section 612. The pivoting of wrist 618 occurs about an axis substantially perpendicular to the longitudinal axis of endoscopic section 612. In the illustration of FIG. 55, wrist 618 and movable fingers 620 are shown in general alignment with the central longitudinal axis of endoscopic section 612 and pivoted outward as shown in phantom lines to illustrate a range of movement.

B. THE HANDLE PORTION

Referring now to FIGS. 55-58, handle portion 610 of closure device 600 includes manual grip 624 and a pivotable trigger, such as wrist lever 626, which is pivoted toward and away from manual grip 624. Wrist lever 626 is pivoted away from manual grip 624 to move wrist 618 and fingers 620 away from fingers 622. Wrist lever 626 is moved toward manual grip 624 to move wrist 618 and fingers 620 such that fingers 620 are generally in line with the central longitudinal axis of endoscopic section 612. The configuration of stent assembly closing device 600 as shown in FIG. 55, i.e. with wrist 618 pivoted such that fingers 620 are in line with the central longitudinal axis of endoscopic section and fingers 620 and 622 are in the closed position, facilitates insertion

19 and removal of stent assembly closing device 600 into or out from an appropriately sized trocar cannula, respectively, so as to allow endoscopic access to the surgical site.

Figure 56:
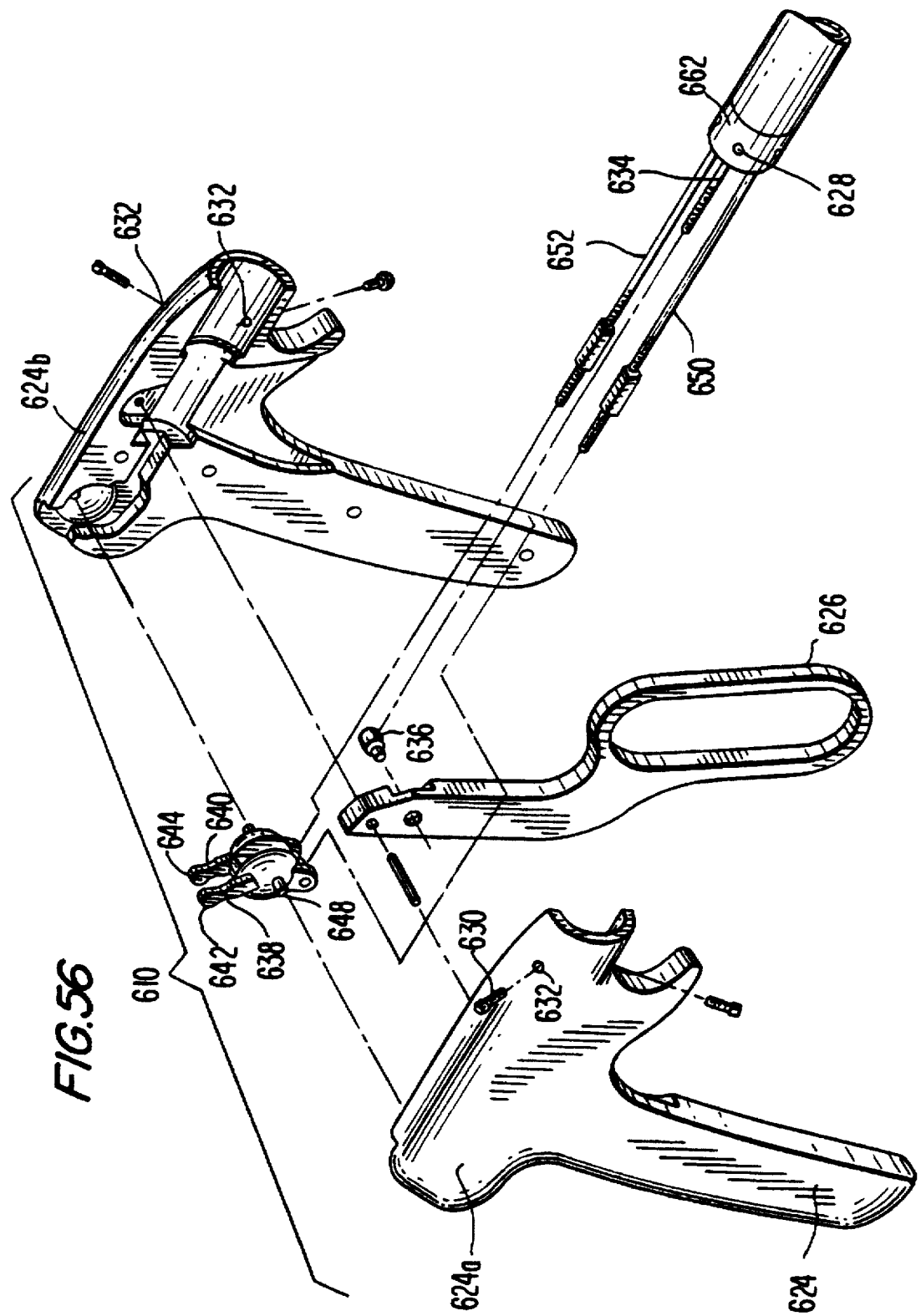
FIG. 56 is an exploded perspective view of the handle portion of the closure device.
Figure 57:
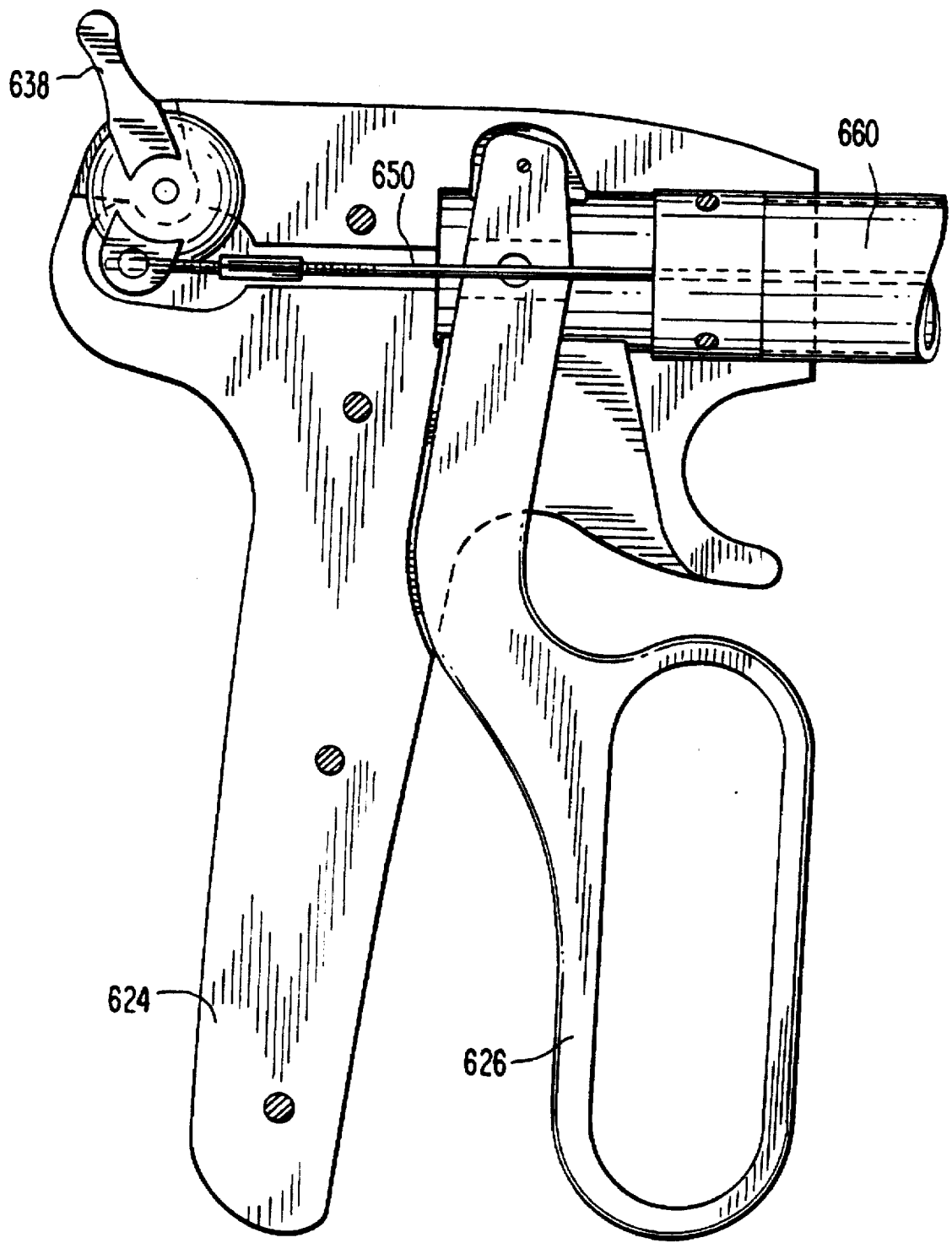
FIG. 57 is a view of the inside of the left side handle area of the closure device with the right half-section of the handle cover removed.

Handle portion 610 is shown in exploded perspective view with parts separated in FIG. 56 and includes an outer housing preferably formed of separate sections 624a and 624b as shown, preferably of polycarbonate material. The separate parts shown are preferably attached by welding, adhesives, etc. The ultimate purpose of handle portion 610 is to provide controlled operation, from the proximal end, of the various functional members located at distal end 614 of stent assembly closing device 600.

Figure 62:
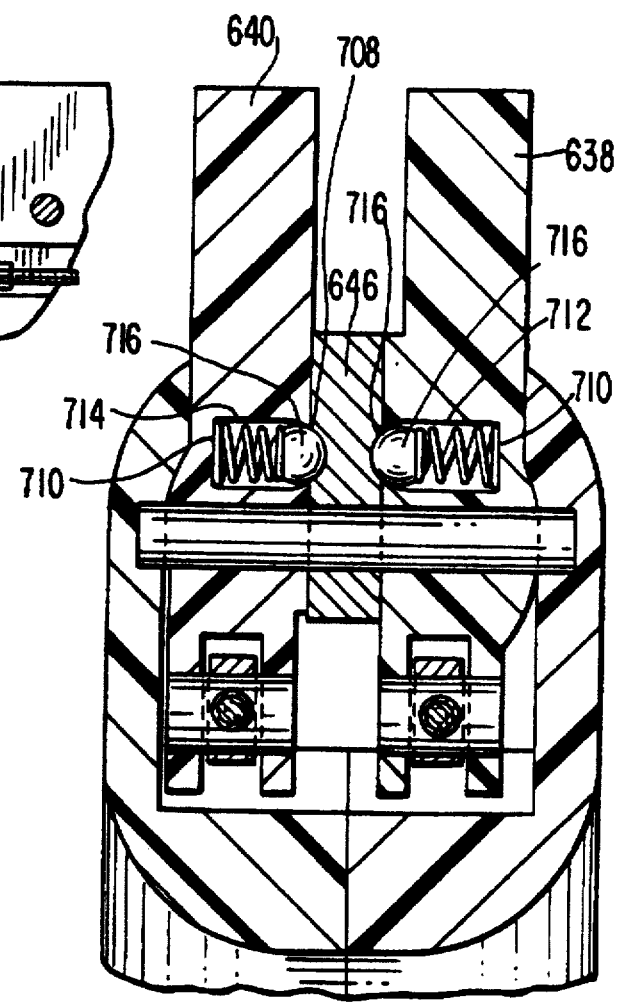
FIG. 62 is a partial cross-sectional view taken along line 62—62 of FIG. 61, which shows some of the details of the toggles and the detent actions of the left and right toggles.

Wrist lever 626 is pivotably mounted in handle portion 610 and is connected to wrist push rod 634 by pivotable mounting pin 636 being slip fit into a bore formed on an upper portion of wrist lever 626. Closure and opening of fingers 620 and fingers 622 at the distal end is accomplished by rotation of first toggle 638 and second toggle 640, respectively. First toggle 638 and second toggle 640 are provided with actuation levers 642 and 644, respectively, which are readily activated by the thumb or index finger of the operator. In order to provide space between actuation levers 642 and 644, a block of filler material such as spacer member 646 (FIG. 62) is provided between first toggle 638 and second toggle 640. In this manner, the operator may independently operate either first toggle 638 or second toggle 640, thereby opening or closing movable fingers 620 or movable fingers 622 independently.

The finger closure control sub-assembly, formed by first toggle 638, spacer member 646 and second toggle 640, each being rotatably mounted on pin 648, is rotatably mounted in a cavity formed in the proximal section of manual grip 624 by recesses molded into each of split half-sections 624a and 624b. Pin 648 is friction fit into bores formed in each split half-section 624a and 624b. when mounted in manual grip 624, actuation levers 642 and 644 project outwardly from manual grip 624 through an opening formed in the proximal end thereof by a recessed portion cut into each of split half-sections 624a and 624b.

Figure 58:
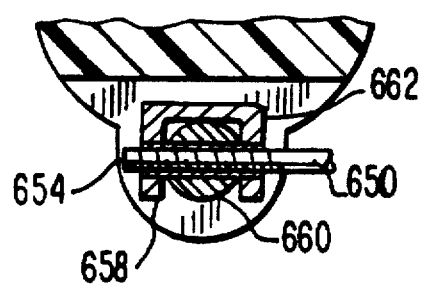
FIG. 58 is a partial cross-sectional view, which shows the mounting of a finger push rod to a toggle.

First toggle 638 and second toggle 640 are operatively connected to first push rod 650 and second push rod 652, respectively. Any suitable connecting means may be utilized. For example, as shown in FIG. 58, threaded end portions 654 and 656 of push rods 650 and 652, respectively, are threaded into rod bearings 658 which are slip fit in pivots 660. Retaining yokes 662 straddle pivots 660 and extend downwardly therefrom from each of first toggle 638 and second toggle 640. As shown in FIG. 56, each of the various push rods, namely, wrist push rod 634 and finger push rods 650 and 652 extend into outer tube 660 of endoscopic section 612 through end plug 662. The various push rods pass through endoscopic section 612 and emerge therefrom through bore holes formed in a flange portion of end plug 664 (FIG. 59) disposed in the distal end portion of outer tube 660 of endoscopic section 612.

C. THE ENDOSCOPIC SECTION

In the embodiment shown, endoscopic section 612 is intended to be permanently attached to handle portion 610. FIG. 56 shows suitable fastening means such as threaded bore holes 628 receiving screws 630 passing through bores 632 formed in split half-sections 624a and 624b of manual grip 624. The device shown is contemplated to be entirely disposable, although it is within the scope of the invention to make the device reusable. For example, it is also contemplated and considered to be within the scope of the invention to construct the endoscopic section to be selectively detachable whereby the handle portion may be sterilized and reused. In an alternative embodiment, the wrist and finger mechanism can be made selectively detachable and disposable so that the handle portion and the remainder of the endoscopic section can be sterilized and reused.

Figure 59:
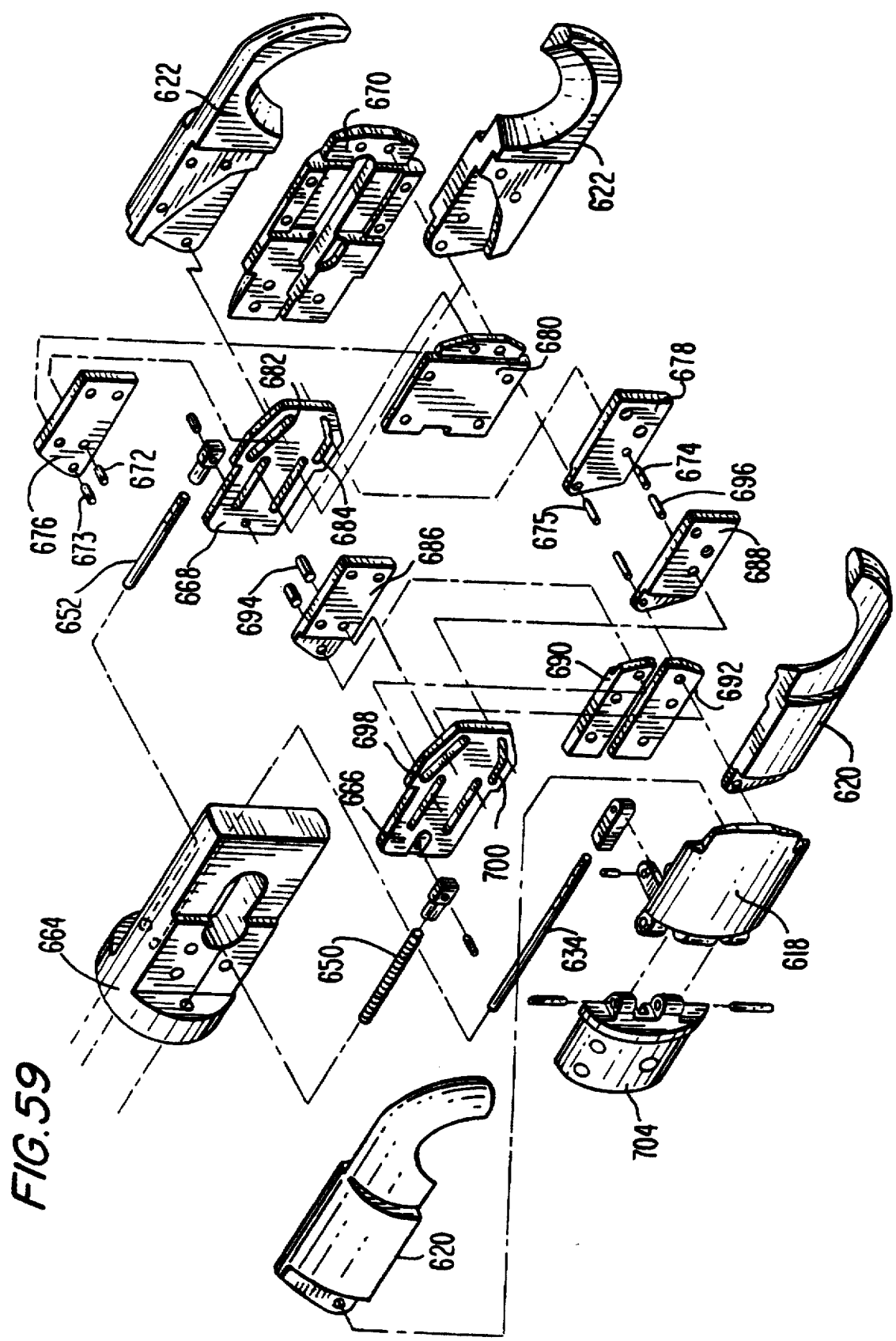
FIG. 59 is an exploded perspective view of the wrist and the finger mechanisms of the closure device.

As shown in FIG. 59, first and second push rods 650 and 652 extend through end plug 664 which is securely mounted in the distal end of outer tube 660. First and second push rods 650 and 652 are operatively connected to slide plates 666 and 668 respectively. Fingers 620, 622 are distal of outer tube 660 and functionally attached to end plug 664. Fingers 622 are pivotably attached to arm 670 by pins 673 and 675. Arm 670 is securely fastened to end plug 664. Slide plate 668 is operatively connected to fingers 622, such as for example by slide plate 668 being mounted between cover plates 676, 678 and 680 on one side and arm 670 on the other side. Closure of fingers 622 is controlled by camming pins 672 and 674 sliding in camming slots 682 an 684, respectively. Camming slot 682 is preferably a straight diagonal camming slot which translates to continuous closure of finger 622 which is operatively connected thereto. Camming slot 684 is operatively connected to finger 622 and is configured to cause finger 622 to open or close for an initial travel portion of camming pin 674 and camming slot 684 and to remain in a fixed closure position for a remainder of the travel of camming pin 674 in camming slot 684.

Sliding plate 666 is operatively connected to fingers 620 in the same fashion as described for sliding plate 668. That is, sliding plate 666 is mounted between cover plates 686, 688, 690, and 692 with camming pins 694 and 696 traveling in camming slots 698 and 700, respectively, to provide the same motion for fingers 620 as described for fingers 622. However, fingers 620 are pivotably mounted to wrist 618, which is pivotably connected to arm 704. Wrist 618 is operatively connected to push rod 634 which upon reciprocating motion causes wrist 618 to pivot with respect to arm 704 and thereby swings fingers 620 as much as about 30° toward and away from the central longitudinal axis of stent assembly closing device 600.

D. OPERATION OF THE CLOSING DEVICE

Operation of the fingers and wrist of stent assembly closing device 600 will now be described with reference to FIGS. 60–67. When stent assembly closing device 600 is inserted into a cannula placed in an incision at the surgical site, fingers 620 and 622 are in their fully closed position as shown in FIG. 63. To position the fingers in the fully closed configuration, first and second toggles 638 and 640 are urged to the position illustrated in FIG. 57. Once stent assembly closing device 600 has been inserted into the surgical site, first and second toggles 638 and 640 may then be urged to the position corresponding open position as shown for fingers 622 in FIG. 64. In this position the fingers are open wider than the diameter of the respective stent-tissue complex so that the stent-tissue complex may be placed within the open fingers.

Figure 60:
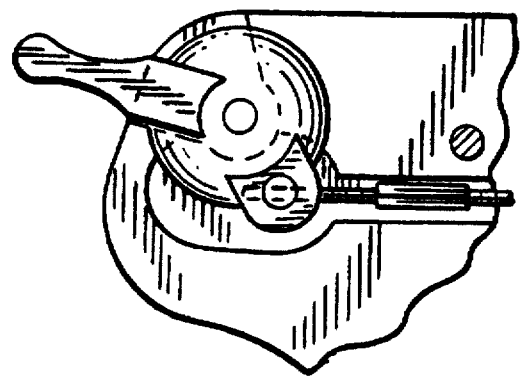
FIG. 60 is a partial view of the right-side finger control lever positioned so that the corresponding fingers are in the completely open position.
Figure 61:
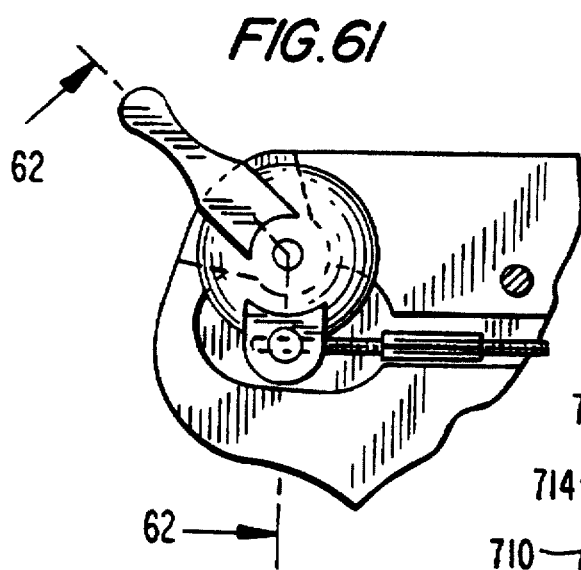
FIG. 61 is a partial view of the right-side finger control lever positioned so that the corresponding fingers are in the holding or clamped position.

When it is desired to grip and join the respective stent-tissue complexes, toggles 638 and 640 are urged from the fully open position as shown in FIG. 60, to the clamped position as shown in FIG. 61. With the toggles in the configuration of FIG. 61, fingers 620 and 622 are positioned as shown in FIG. 65 for finger 622. In this position, fingers 622 and 620 are closed about the stent-tissue complexes. To prevent fingers 620 and 622 from opening when the stent-tissue complexes are joined, spacer member 646 is preferably provided with positioning means. The positioning means may include rounded depressions, i.e. detents 706 and 708, and springs 710 disposed within chambers 712 and 714 formed in each of the toggles 638 and 640, respectively. Each spring 710 is biased against a ball bearing 716, or the like, which seats in the respective rounded depression 706 formed on each side of spacer member 646.

Figure 66:
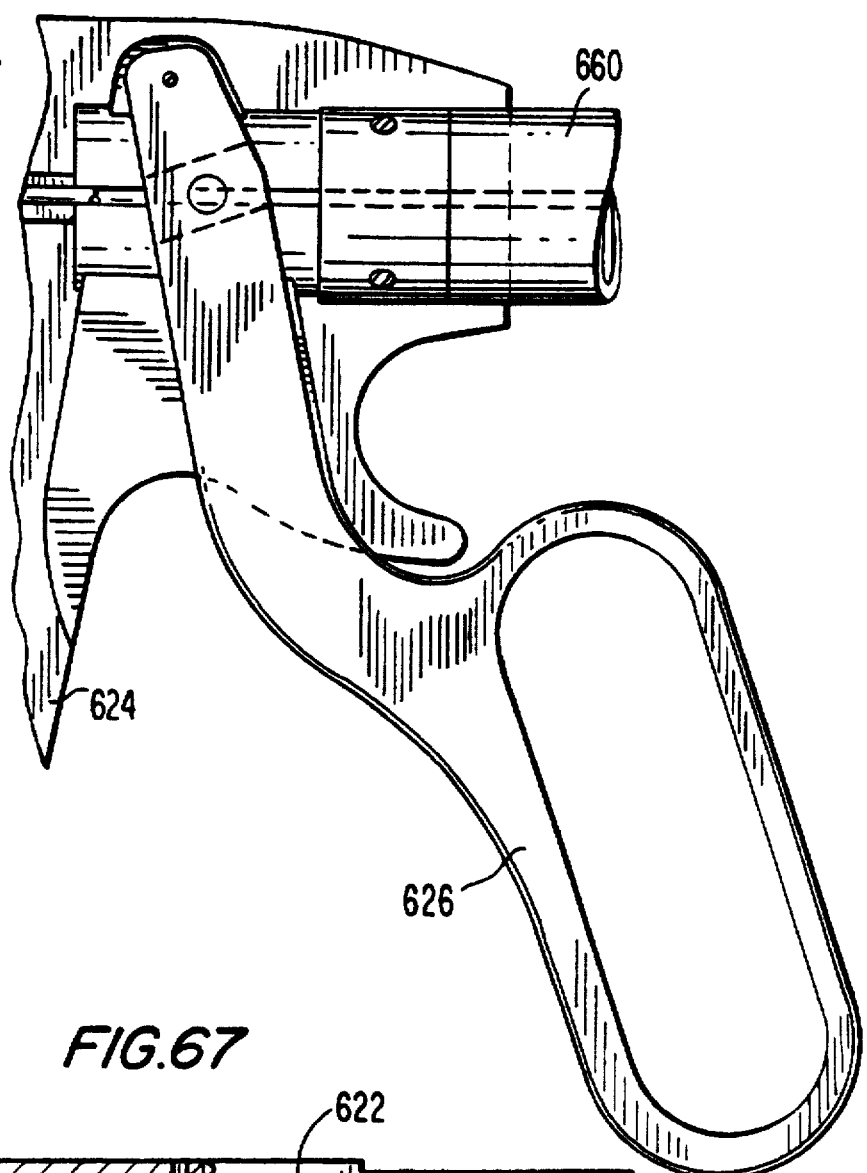
FIG. 66 is a partial view of the closure device handle portion with the wrist lever in the forward position.
Figure 67:
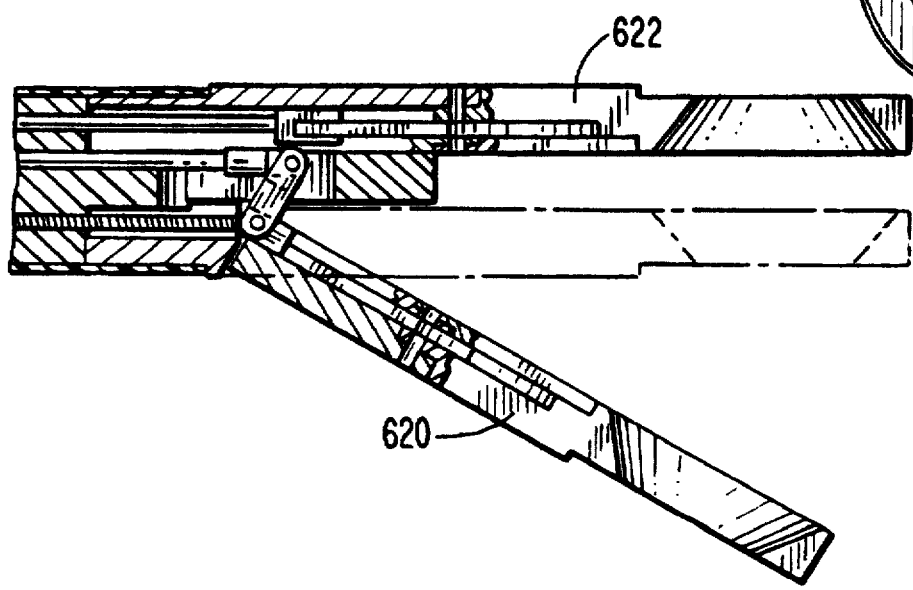
FIG. 67 is a partial cross-sectional view of the distal end of the closing device, which shows the right gripping fingers shifted outwardly by the wrist member when the wrist lever is moved forward.

As shown in FIG. 66, to operate wrist 618, wrist lever 626 is pivoted away from manual grip 624 driving wrist push rod 634 distally which causes wrist 618 to pivot outwardly from arm 704 into an open position. To close wrist 618, wrist lever 626 is pivoted toward manual grip 624 thereby pulling wrist push rod 634 in a proximal direction and causing wrist 618 to pivot inwardly towards the central longitudinal axis of stent assembly closing device 600 until finger 620 are positioned as shown in phantom lines in FIG. 67.

E. USE OF THE CLOSING DEVICE

Figure 68:
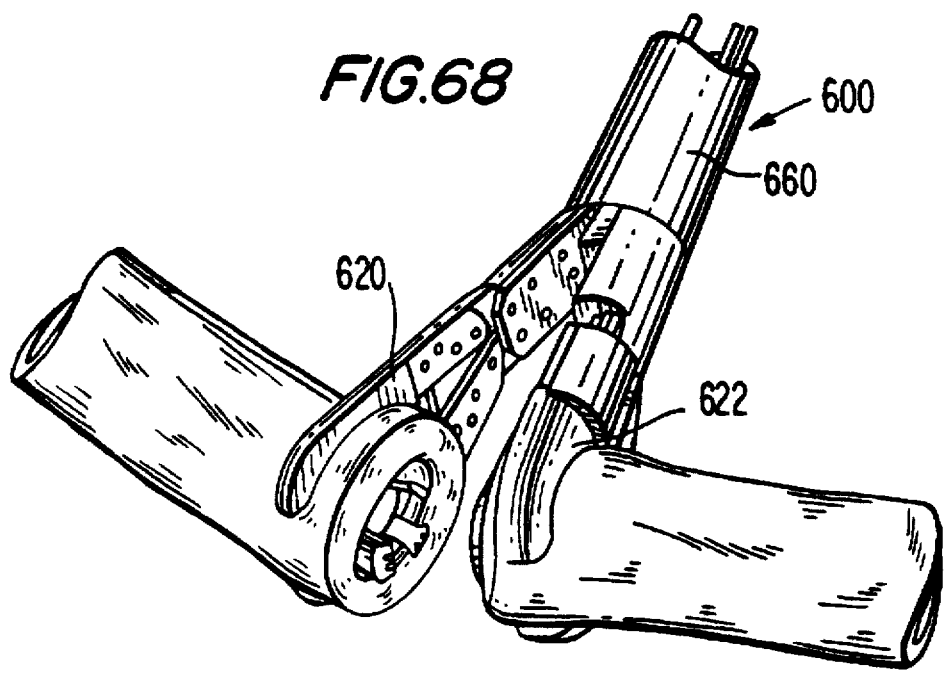
FIG. 68 is a perspective view of the distal end of the stent closing device, which shows the fingers clamped about the two sections of the organ to be joined.
Figure 69:
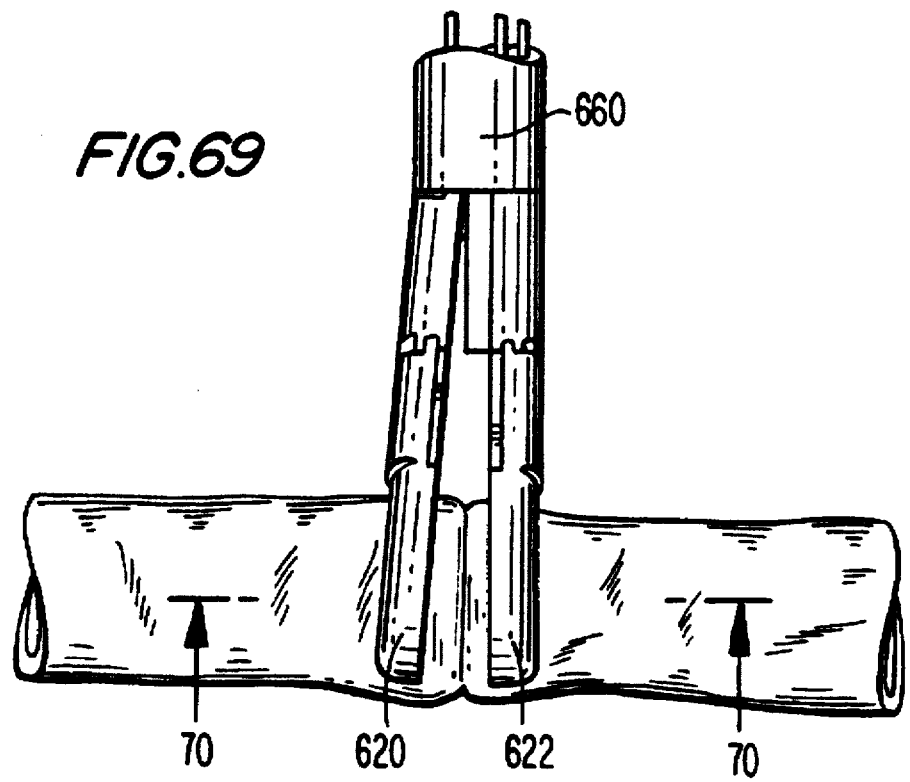
FIG. 69 is a top plan view where the wrist is in a closed position.

In use, once the stent-tissue complexes have been formed by stent applicator instrument 400, stent assembly closing device 600 is inserted down through the cannula and fingers 620 and 622 are opened to their fully opened position by moving toggles 638 and 640. The stent tissue complexes are then placed within the opened fingers and the stent toggles urged to their clamped position as shown in FIG. 61, thereby locking fingers 620 and 622 about the end portions of the stent-tissue complexes as shown in FIG. 68. Once the fingers are in a clamped position, wrist lever 626 is pivoted toward manual grip 624 bringing the two ends of the opposing stent-tissue complexes together as shown in FIG. 69 and 70. In FIG. 70 locking means such as male axle 216 is shown mated with locking means such as female axle 218 as the wrist is urged to the closed position thereby completing the anastomosis.

V. THE KIT

The present invention is readily adaptable to be provided to surgeons in the form of a kit in which all necessary equipment and accessories are provided in sterile form ready for use in surgery. For example, the stent applicator instrument 440, the trocar adapter and the stent assembly closing device 600 of the present invention can be readily packaged with a supply of stent assembly components sufficient to assemble at least one male and female stent half-portion. The different instruments and components may be provided separately, as a matched kit or in a blister or other type package, suitable and ready for use by the surgeon and the surgeon's assistants. The instruments and stent components can be provided in any size matched to meet the needs of the particular anastomosis to be performed.

In addition, the kit can include a matching trocar assembly (not shown) with appropriate valve assembly to prevent loss of the insufflating gas from the peritoneum between the trocar and the outside surface of the endoscopic section. The outer housing of the endoscopic section is substantially closed at the point of attachment of either the stent holding and placing assembly on the stent applicator instrument and the wrist and finger mechanism of the stent closing device. Thus, release of insufflating gases through these distal end mechanisms and the endoscopic section housing is either non-existent or minimal. Such a trocar assembly is available from United States Surgical Corporation, Norwalk, Conn., under the trademark SURGIPORT brand trocar assembly. See also U.S. Pat. No. 5,116,353 to Green which is hereby incorporated herein by reference.

While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. A surgical instrument for carrying and attaching separate components of a compression anastomosis device to the end of tissue of a tubular hollow organ, comprising:
   (a) an elongated housing having a proximal end and a distal end;
   (b) first and second compression anastomosis device components adapted to interlock with each other to form one side of a compression anastomosis assembly on the end of one section of a tubular hollow organ at least one of the first and second compression anastomosis device components including a mating surface configured and dimensioned to contact a further anastomosis device component;
   (c) supporting means operatively associated with said distal end of said elongated housing, for supporting said first and second compression anastomosis device components; and
   (d) assembling means associated with said supporting means and operable from said proximal end of said elongated housing, for assembling said first and second compression anastomosis device components within tubular body tissue.

2. A surgical instrument according to claim 1, further comprising actuating means operatively connected to said proximal end of said elongated housing, for selectively actuating said assembling means such that said assembling means travels a predetermined distance in a first direction and then travels a predetermined distance in a second direction.

3. A surgical instrument according to claim 1, further comprising: a third compression anastomosis device component; and
   driving means associated with said distal end of said elongated housing, for driving said third compression anastomosis device component into said assembled first and second compression anastomosis device components.

4. A surgical instrument according to claim 3, further comprising actuating means operatively connected to said proximal end of said elongated housing, for selectively actuating said driving means.

5. A surgical instrument according to claim 3, further comprising first and second actuating means operatively connected to said proximal end of said elongated housing, for selectively actuating said assembling means and said driving means, respectively.

6. A surgical instrument according to claim 1, further comprising cutting means operatively mounted at said distal end of said elongated housing, for selectively cutting away excess tissue.

7. A surgical instrument according to claim 1, wherein said supporting means includes at least one retaining portion for releasably retaining at least one of said compression anastomosis device components.

8. A surgical instrument according to claim 7, wherein said retaining portion includes at least one expandable member movable between a holding position and a released position, said expandable member being configured and dimensioned to releasably retain at least one of said compression anastomosis device components.

9. A surgical instrument according to claim 8, wherein said at least one expandable member includes a plurality of radially expandable elements.

10. A surgical instrument according to claim 8, further comprising release control means operable from said proximal end of said elongated housing, for controlling said at least one expandable member between said holding position and said released position.

* * * * *